(12) United States Patent
Capcelea et al.

(10) Patent No.: US 8,782,884 B2
(45) Date of Patent: Jul. 22, 2014

(54) MANUFACTURING AN ELECTRODE ASSEMBLY HAVING CONTOURED ELECTRODE CONTACT SURFACES

(75) Inventors: Edmond D. Capcelea, Bondi Junction (AU); Peter Gibson, South Coogee (AU); Fysh Dadd, Lane Cove (AU)

(73) Assignee: Cochlear Limited, Macquarie University, NSW (AU)

( * ) Notice: Subject to any disclaimer, the term of this patent is extended or adjusted under 35 U.S.C. 154(b) by 260 days.

(21) Appl. No.: 12/628,848

(22) Filed: Dec. 1, 2009

(65) Prior Publication Data

US 2011/0126410 A1 Jun. 2, 2011

(51) Int. Cl.
*H01R 43/24* (2006.01)
*B23P 19/00* (2006.01)

(52) U.S. Cl.
USPC .................. 29/884; 29/746; 29/885; 29/831; 29/848; 29/849

(58) Field of Classification Search
CPC . H01R 43/005; A61N 1/0541; B29C 45/0055
USPC ........... 29/884, 885, 746, 830, 831, 832, 852; 607/137, 116, 115, 117, 57; 219/121.69; 381/151
See application file for complete search history.

(56) References Cited

U.S. PATENT DOCUMENTS

| | | |
|---|---|---|
| 3,749,101 A | 7/1973 | Williamson |
| 3,902,078 A | 8/1975 | Peterson |
| 4,502,492 A | 3/1985 | Bornzin |
| 4,532,930 A | 8/1985 | Crosby et al. |
| 5,000,194 A * | 3/1991 | van den Honert et al. .... 607/137 |
| 5,118,400 A | 6/1992 | Wollam |
| 5,433,836 A | 7/1995 | Martin et al. |
| 5,628,778 A | 5/1997 | Kruse et al. |
| 5,659,237 A | 8/1997 | Divan et al. |

(Continued)

FOREIGN PATENT DOCUMENTS

| | | |
|---|---|---|
| EP | 0175654 | 3/1986 |
| WO | 00/71063 | 11/2000 |

(Continued)

OTHER PUBLICATIONS

Fukami et al., "Ablation of Silicone Rubber Using UV-Nanosecond and IR-Femtosecond Lasers", Japanese Journal of Applied Physics, Jul. 7, 2004, 43(7A):4240-4241 (2 pages).

(Continued)

*Primary Examiner* — Peter DungBa Vo
*Assistant Examiner* — Kaying Kue

(57) ABSTRACT

A method for manufacturing an electrode assembly. The method comprises: forming a comb having a plurality of electrode contacts, wherein the surface of at least one of the electrode contacts comprises a plurality of indentations such that the effective surface area per area unit of a center region of the at least one electrode contact is larger than the effective surface area per area unit of the of the region of the surface outside the center region; assembling an array of electrode contacts from the comb; molding a carrier member about the assembled array of electrode contacts, wherein a surface of the at least one electrode contact is covered by a layer of the carrier member material; and removing the layer of carrier member material on the surface of the at least one electrode contact.

30 Claims, 19 Drawing Sheets

(56) References Cited

U.S. PATENT DOCUMENTS

| | | | |
|---|---|---|---|
| 5,810,725 A * | 9/1998 | Sugihara et al. | 600/372 |
| 6,043,628 A | 3/2000 | Perelle et al. | |
| 6,078,165 A | 6/2000 | Ashtiani et al. | |
| 6,144,883 A | 11/2000 | Kuzma | |
| 6,304,787 B1 | 10/2001 | Kuzma et al. | |
| 6,340,879 B1 | 1/2002 | Bläcker | |
| 6,421,569 B1 | 7/2002 | Treaba et al. | |
| 6,430,448 B1 | 8/2002 | Chitre et al. | |
| 6,553,742 B2 * | 4/2003 | Spatafora | 53/466 |
| 6,757,970 B1 * | 7/2004 | Kuzma et al. | 29/847 |
| 6,862,805 B1 | 3/2005 | Kuzma et al. | |
| 6,968,238 B1 * | 11/2005 | Kuzma | 607/137 |
| 7,319,906 B2 * | 1/2008 | Kuzma et al. | 607/137 |
| 7,463,400 B1 | 12/2008 | Tatsuura et al. | |
| 7,555,352 B2 * | 6/2009 | Dadd et al. | 607/137 |
| 7,974,712 B2 * | 7/2011 | Gibson et al. | 607/137 |
| 7,991,475 B1 * | 8/2011 | Tang et al. | 607/45 |
| 8,301,269 B2 * | 10/2012 | Gibson et al. | 607/137 |
| 8,461,042 B2 * | 6/2013 | Dadd et al. | 438/633 |
| 2002/0137243 A1 | 9/2002 | Chen et al. | |
| 2004/0256146 A1 | 12/2004 | Frericks et al. | |
| 2005/0020463 A1 | 1/2005 | Ikemoto et al. | |
| 2006/0004432 A1 | 1/2006 | Parker et al. | |
| 2006/0020318 A1 | 1/2006 | Lenarz et al. | |
| 2006/0213881 A1 | 9/2006 | Oliphant et al. | |
| 2006/0236532 A1 | 10/2006 | Schuller | |
| 2007/0127745 A1 * | 6/2007 | Gibson et al. | 381/151 |
| 2009/0043358 A1 | 2/2009 | Dadd et al. | |
| 2009/0068598 A1 | 3/2009 | Murase et al. | |
| 2009/0081325 A1 | 3/2009 | Kitamura et al. | |
| 2009/0168391 A1 | 7/2009 | Saitou et al. | |
| 2009/0204177 A1 | 8/2009 | Parker et al. | |
| 2009/0229739 A1 | 9/2009 | Schuller | |
| 2010/0063569 A1 | 3/2010 | Tockman et al. | |
| 2010/0102715 A1 | 4/2010 | Suh | |
| 2011/0126410 A1 * | 6/2011 | Capcelea et al. | 29/885 |
| 2011/0130815 A1 * | 6/2011 | Gibson et al. | 607/116 |

FOREIGN PATENT DOCUMENTS

| | | |
|---|---|---|
| WO | 01/83855 | 11/2001 |
| WO | 02/087685 | 11/2002 |
| WO | 02/089907 | 11/2002 |
| WO | 2005/004978 | 1/2005 |
| WO | 2006/000031 | 1/2006 |
| WO | 2009/065127 | 5/2009 |

OTHER PUBLICATIONS

PCT/AU2004/000920 , "International Preliminary Report on Patentability", Jan. 9, 2006, 5 pages.

PCT/AU2004/000920 , "International Search Report", Nov. 17, 2004, 3 pages.

PCT/AU2004/000920 , "Written Opinion", Nov. 17, 2004, 4 pages.

* cited by examiner

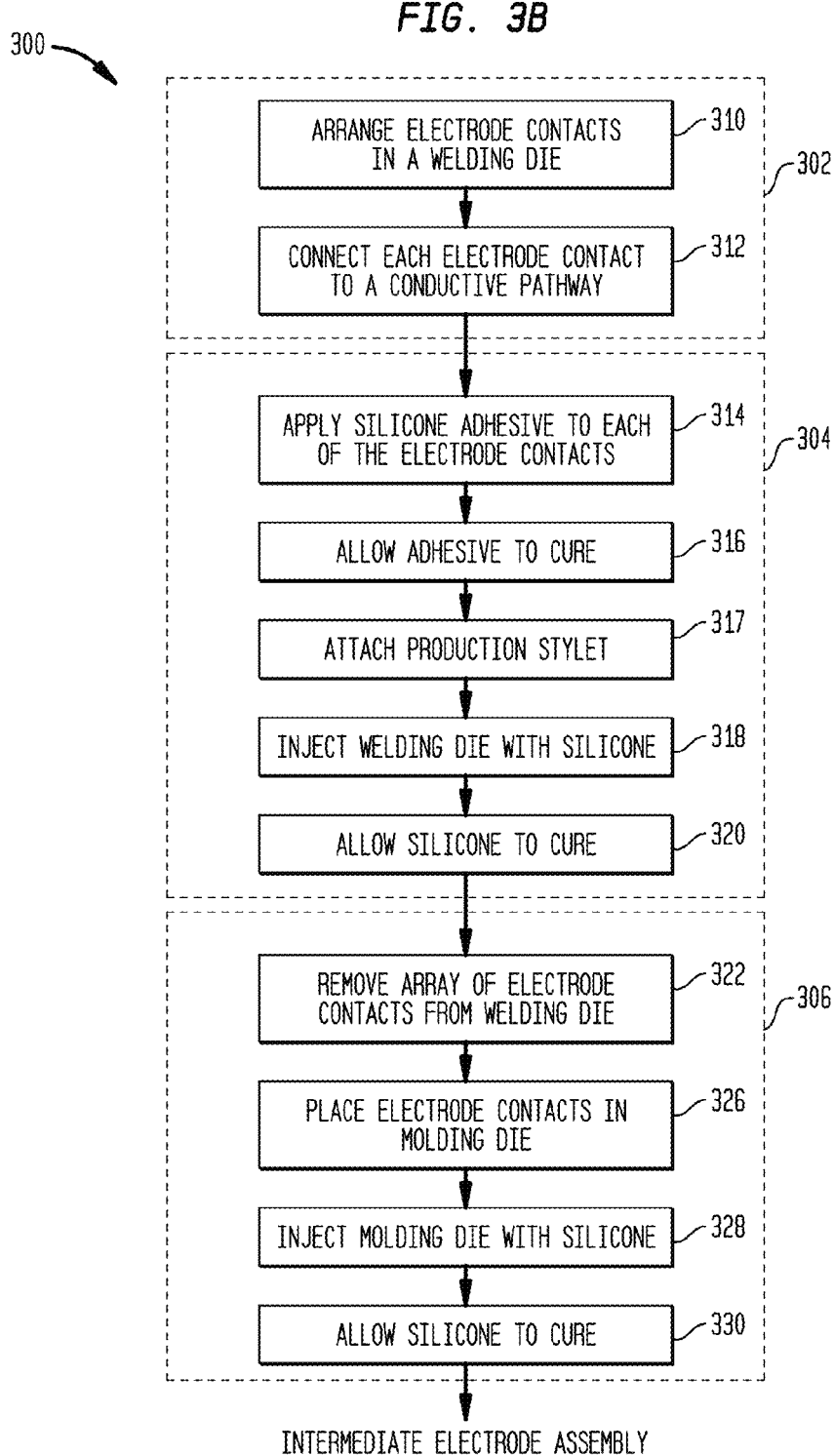

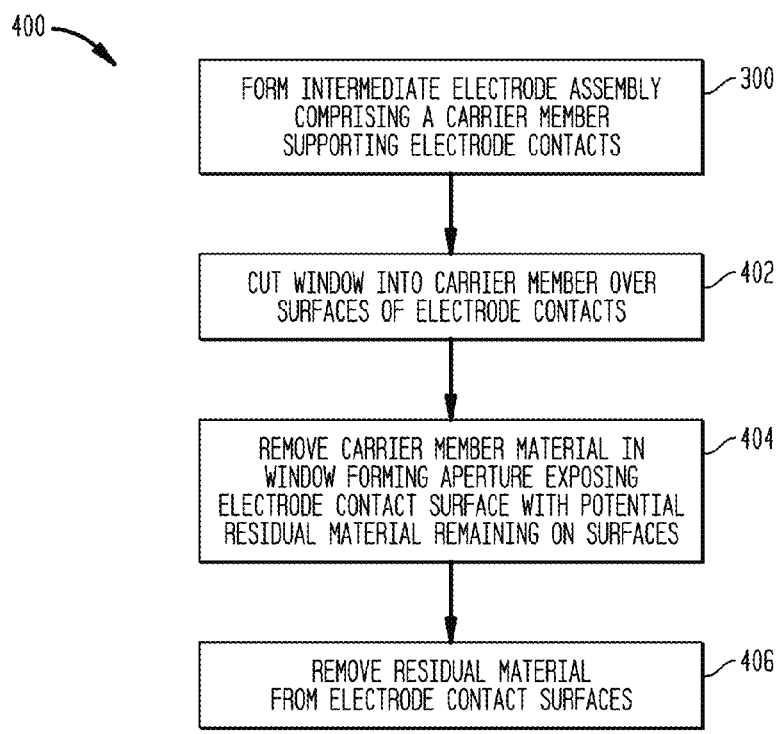

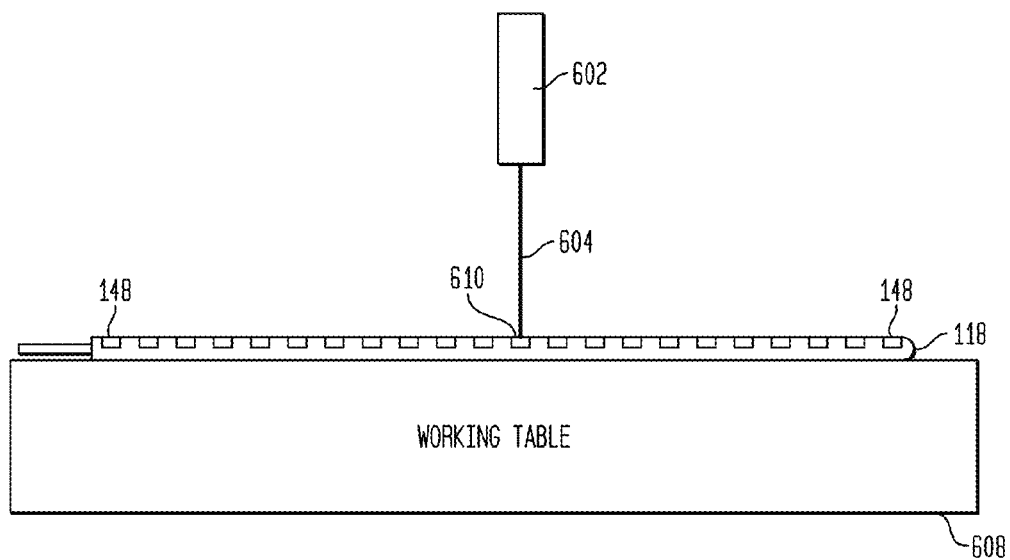

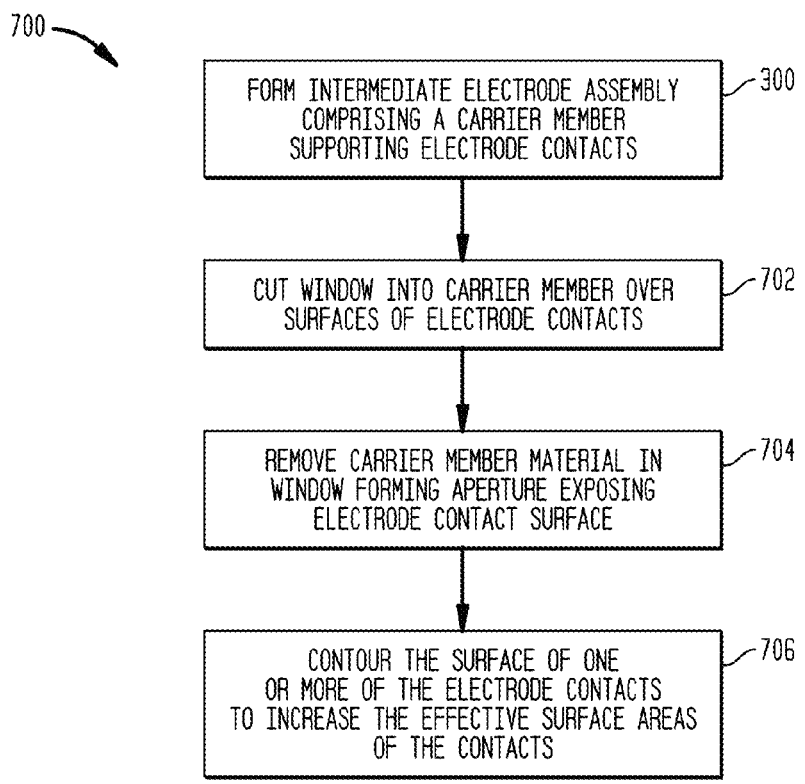

MANUFACTURING AN ELECTRODE ASSEMBLY HAVING CONTOURED ELECTRODE CONTACT SURFACES

CROSS-REFERENCE TO RELATED APPLICATIONS

This application is related to commonly owned and co-pending U.S. Utility Patent Application entitled "CONTOURED ELECTRODE CONTACT SURFACES," filed Dec. 1, 2009; U.S. Utility Patent Application entitled "ELECTRODE CONTACT CONTAMINATE REMOVAL," filed Dec. 1, 2009; U.S. Utility patent application Ser. No. 11/59,256, entitled "METHODS FOR MAINTAINING LOW IMPEDENCE ELECTRODES," filed Jun. 23, 2005; and U.S. Utility patent application Ser. No. 12/423,562, entitled "MAINTAINING LOW IMPEDENCE OF ELECTRODES," filed Apr. 14, 2009. The content of these applications are hereby incorporated by reference herein.

BACKGROUND

1. Field of the Invention

The present invention relates generally to electrically stimulating medical devices having electrode contacts, and more particularly to manufacturing an electrode assembly having contoured electrode contact surfaces.

2. Related Art

A variety of implantable medical devices have been proposed to deliver controlled electrical stimulation to a region of a subject's body to achieve a therapeutic effect. Such devices, generally referred to herein as electrically-stimulating medical devices, include muscle or tissue stimulators, brain stimulators (deep brain stimulators, cortical stimulators, etc.), cardiac pacemakers/defibrillators, functional electrical stimulators (FES), spinal cord stimulators (SCS), pain stimulators, electrically-stimulating hearing prostheses, etc. Such electrically-stimulating medical devices include one or more electrode contacts which deliver electrical stimulation signals to the subject (commonly referred to as a patient, recipient, etc.; "recipient" herein). In addition, the electrically-stimulating medical devices may also include one or more electrode contacts to monitor and/or measure a particular biological activity, sometimes broadly referred to as sensors.

Electrically-stimulating hearing prostheses are typically used to treat sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from hearing prostheses that generate mechanical motion of the cochlea fluid. Such individuals may benefit from electrically-stimulating hearing prostheses that deliver electrical stimulation to nerve cells of the auditory system. As used herein, a recipient's auditory system includes all sensory system components used to perceive a sound signal, such as hearing sensation receptors, neural pathways, including the auditory nerve and spiral ganglion, and the regions of the brain used to sense sounds. Electrically-stimulating hearing prostheses include, but are not limited to, auditory brain stimulators and cochlear implants.

Cochlear implants are often utilized when a recipient's sensorineural hearing loss is due to the absence or destruction of the cochlear hair cells which transduce acoustic signals into nerve impulses. Cochlear implants generally include an electrode assembly implanted in the cochlea. The electrode assembly includes a plurality of electrode contacts which deliver electrical stimulation signals to the auditory nerve cells, thereby bypassing absent or defective hair cells. The electrode contacts of the electrode assembly differentially activate auditory neurons that normally encode differential pitches of sound.

Auditory brain stimulators are often proposed to treat a smaller number of individuals with bilateral degeneration of the auditory nerve. For such recipients, an auditory brain stimulator comprises an electrode assembly implanted in the cochlear nucleus of the brainstem. The electrode contacts of the electrode assembly provide electrical stimulation signals directly to the cochlear nucleus.

SUMMARY

In one aspect of the present invention a method for manufacturing an electrode assembly is provided. The method comprises: contouring the surface of at least one electrode contact; depositing a protective coating on the contoured surface; molding a carrier member about the array of electrode contacts, wherein the contoured surface of the at least one electrode contact is covered by a layer of the carrier member material; and removing the protective coating and the layer of carrier member material on the surface of the at least one electrode contact.

In another aspect of the present invention a system for manufacturing an electrode assembly is provided. The system comprises: means for contouring the surface of at least one electrode contact; means for depositing a protective coating on the contoured surface; means for molding a carrier member about the array of electrode contacts, wherein the contoured surface of the at least one electrode contact is covered by a layer of the carrier member material; and means for removing the protective coating and the layer of carrier member material on the surface of the at least one electrode contact.

BRIEF DESCRIPTION OF THE DRAWINGS

Embodiments of the present invention are described below with reference to the attached drawings, in which:

FIG. 3B is a detailed flow chart illustrating the process for forming an intermediate electrode assembly in accordance with embodiments of FIG. 3A;

FIG. 4 is a flowchart illustrating a method for treating the surface of an electrode contact to remove residual carrier member material, in accordance with embodiments of the present invention;

FIG. 6 is a schematic diagram illustrating the treating of the surface of an electrode contact, in accordance with embodiments of the present invention;

FIG. 7 is a flowchart illustrating a method for forming an electrode assembly having contoured electrode contact surfaces, in accordance with embodiments of the present invention;

DETAILED DESCRIPTION

Figure 1:
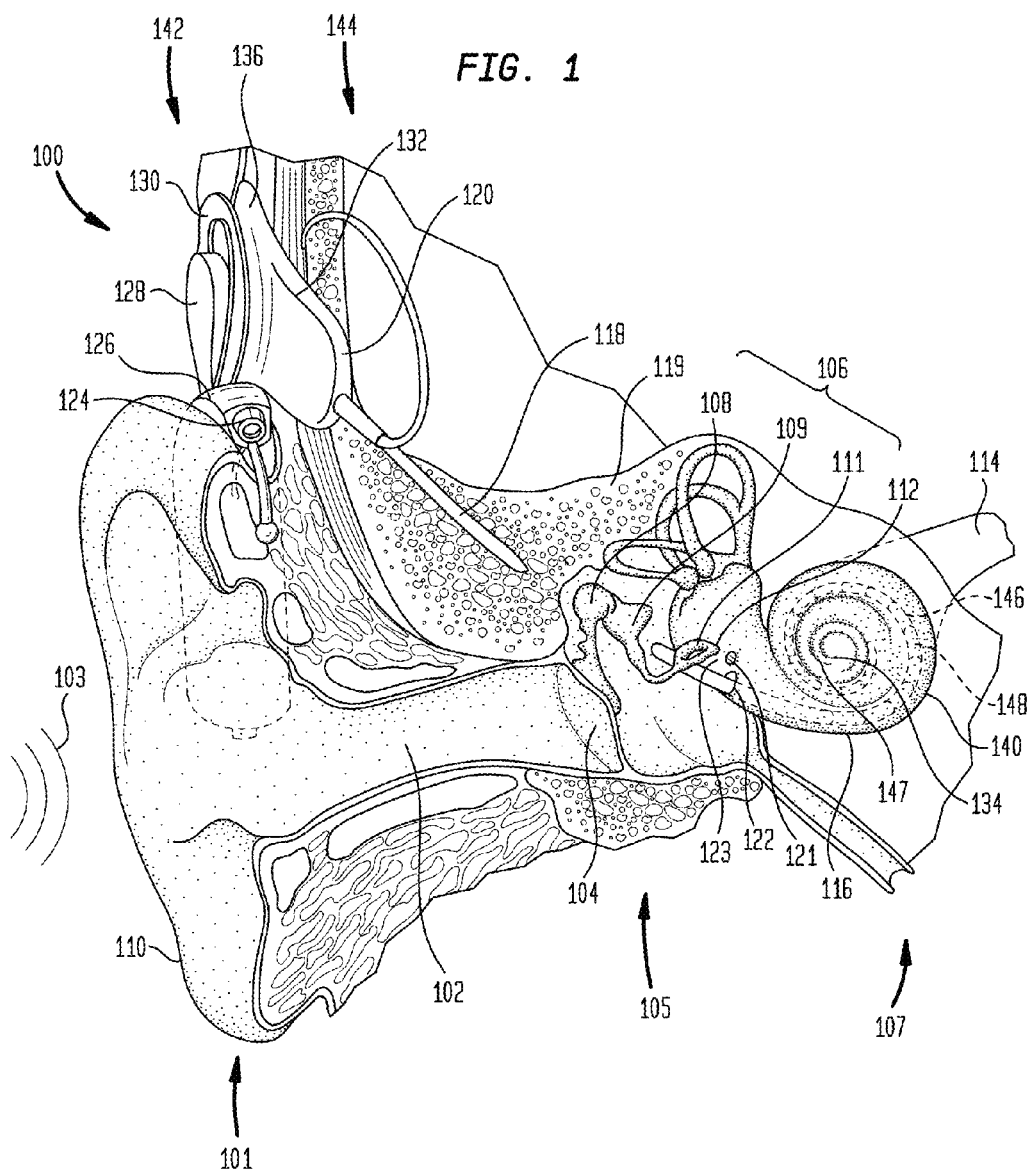
FIG. 1 is a perspective view of a cochlear implant in which embodiments of the present invention may be implemented.

Aspects of the present invention are generally directed to treating the surface of an electrode contact of an electrically-stimulating medical device to increase the effective surface area of the contact without increasing the geometric surface area of the electrode contact. The effective surface area of an electrode contact is the surface area having the ability to deliver electrical stimulation signals to a recipient, while the geometric surface area is the planar area bounded by the outer dimensions of the surface, and does not include any fluctuations or changes in the surface.

Increasing the effective surface area of the electrode contact decreases the impedance of the contact which in turn provides several advantages. For example, in certain embodiments the decreased impedance provides improved efficiency of the contact. In other embodiments, the decreased impedance enables a reduction in the geometric area of the contact. These and other advantages are described in greater detail below.

In certain embodiments of the present invention, the effective surface area of an electrode contact is increased by treating the surface of the contact to remove contaminates from the contact surface. Contaminates disposed on the surface of an electrode contact surface may impede or prevent the delivery of electrical stimulation signals via the covered portions, thereby reducing the effective surface area of the electrode contacts. Such contaminants may result from, for example, the manufacturing process. Exemplary contaminates include, but are not limited to, overmolding residuals, contaminates introducing during manufacture of the electrode contact material (i.e. residue from a rolling process), masking materials, adhesives, wash residue remaining after washing cycles or acidic baths, airborne contaminates, or residue remaining from contact between the surface and other materials or chemicals such as lenium, clorofluorocarbons, such as Freon®, etc. As described below, these contaminates may be removed from the contact surfaces at various stages during, (or following) the manufacturing of an electrically-stimulating medical device.

In other embodiments, the effective surface area of an electrode contact is increased by contouring the contact surface. As described below, in certain embodiments of the present invention, an electrode contact may be treated such that different regions of the surface have different contours. By selecting the different contours, the delivery of current from the contact surface may be controlled.

Embodiments of the present invention are described herein primarily in connection with one type of electrically-stimulating medical device, an electrically-stimulating hearing prosthesis, namely a cochlear prosthesis (commonly referred to as cochlear prosthetic devices, cochlear implants, cochlear devices, and the like; simply "cochlea implants" herein.) Cochlear implants deliver electrical stimulation signals to the cochlea of a recipient. Cochlear implants deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically or mechanically stimulate components of the recipient's middle or inner ear. It should be also noted that embodiments may be used with other types of medical devices including, but not limited to, muscle or tissue stimulators, brain stimulators (deep brain stimulators, cortical stimulators, etc.), cardiac pacemakers/defibrillators, functional electrical stimulators (FES), spinal cord stimulators (SCS), pain stimulators, electrically-stimulating hearing prostheses, etc.

FIG. 1 is perspective view of an exemplary cochlear implant, referred to as cochlear implant 100, in which embodiments of the present invention may be implemented. Cochlear implant 100 is shown implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130. Electrode assembly 118 has a proximal end connected to stimulator unit 120, and a distal end implanted in cochlea 140. Electrode assembly 118 extends from stimulator unit 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrode contacts 148, sometimes referred to as contact array 146 herein. Electrode contacts 148 are formed from a biocompatible metal or metal alloy such as, for example, platinum.

Although array 146 of electrode contacts 148 may be disposed on electrode assembly 118, in most practical applications, array 146 of electrode contacts 148 is integrated into electrode assembly 118. As such, electrode contacts 148 are described herein as being disposed in electrode assembly 118. Stimulator unit 120 generates stimulation signals which are applied by electrode contacts 148 to cochlea 140, thereby stimulating auditory nerve 114. Because, in cochlear implant 100, electrode assembly 118 provides stimulation, electrode assembly 118 is sometimes referred to as a stimulating assembly.

In cochlear implant 100, external coil 130 transmits electrical signals (that is, power and stimulation data) to internal coil 136 via a radio frequency (RF) link. Internal coil 136 is typically a conductive pathway antenna coil comprised of multiple turns of electrically insulated single-strand or multi-strand platinum or gold conductive pathway. The electrical insulation of internal coil 136 is provided by a flexible silicone molding (not shown). In use, implantable receiver unit 132 may be positioned in a recess of the temporal bone adjacent auricle 110 of the recipient.

Figure 2A:
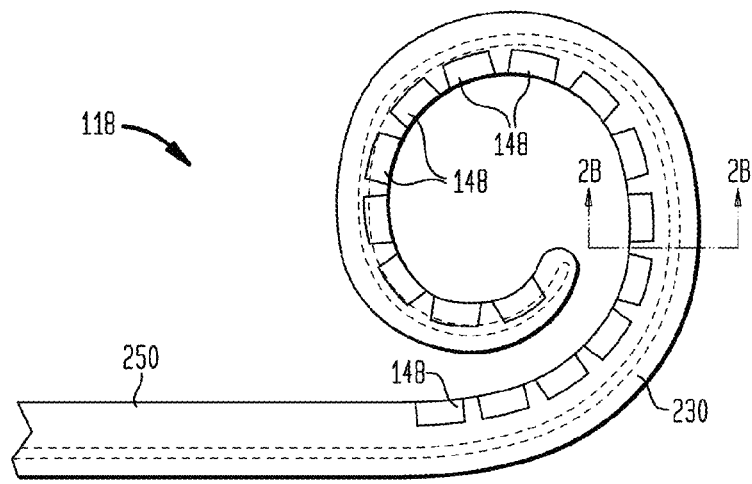
FIG. 2A is a side view of an electrode assembly, in accordance with embodiments of the present invention.
Figure 2B:
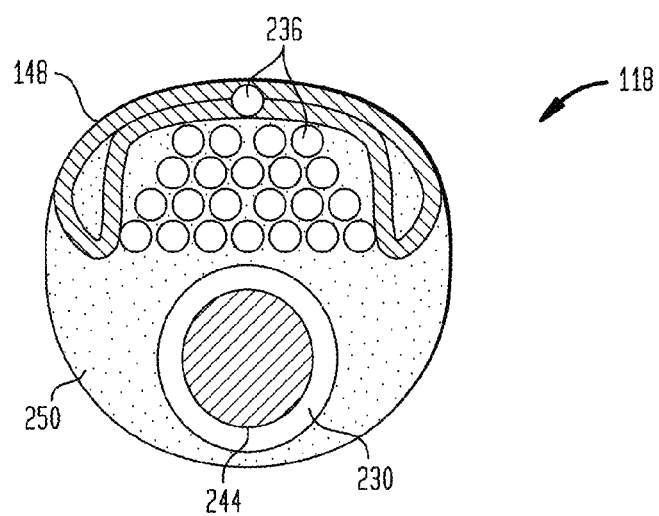
FIG. 2B is a cross-sectional view of the electrode assembly of FIG. 2A taken along section line 2B-2B.

FIGS. 2A and 2B provide simplified views of an embodiment of electrode assembly 118. FIG. 2A is a side view of electrode assembly 118 in its curved position. FIG. 2B is a rotated cross-sectional view of electrode assembly 118 taken along section line 2B-2B in FIG. 2A. As illustrated, electrode assembly 118 comprises a plurality of electrode contacts 148 extending lengthwise along electrode assembly 118 and disposed in a carrier member 250. It would be appreciated that carrier member 250 may be formed from a number of different materials. In one embodiment, carrier member 250 is formed from a silicone such as a Silastic® material (e.g., polydimehtylsiloxane (PDMS)), while in other embodiments carrier member 250 may be in whole, or in part, a urethane, polyimide, polypropelene, polytetrafluoroethene (PTFE), polyaryletheretherketone, (PEEK) or any other type suitable material.

Electrode assembly 118 may further comprise a lumen 230 through which a stiffener or stylet 244 may be placed for use in implantation of electrode assembly 118 in the recipient's cochlea. It would be appreciated that FIG. 2A illustrates embodiments in which stylet 244 has been removed. Each electrode contact 148 may be connected to one or more conductive pathways 236 which extend from the electrode contacts 148 through electrode assembly 118 to stimulator unit 120 (FIG. 1). In certain embodiments, electrode assembly 118 comprises 22 electrode contacts 148, although in other embodiments, electrode assembly 118 may comprise any number of electrode contacts.

As noted, embodiments of the present invention are directed to treating the surface of an electrode contact to increase the effective surface area of the contact. Due to this increased surface area, the contact is configured to deliver larger amounts of current when compared to un-treated contacts As such, electrode assemblies having more electrode contacts may be realized without reducing the ability of any one contact to deliver current.

Figure 3A:
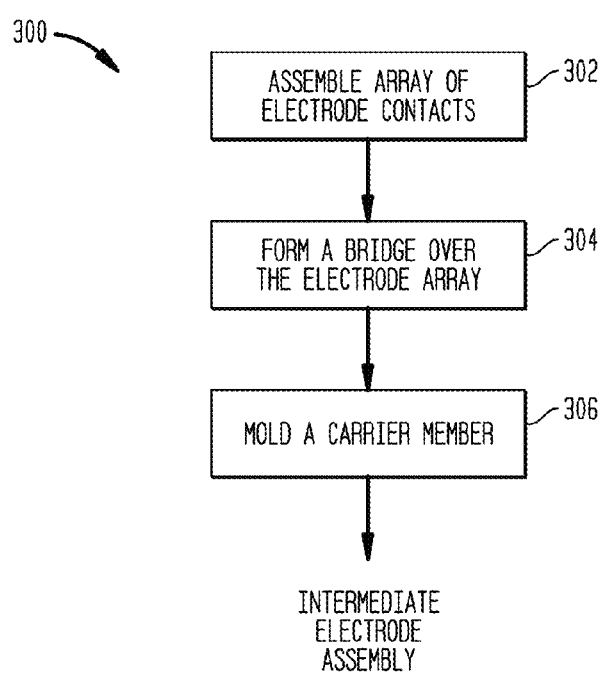
FIG. 3A is a high level flow chart illustrating an exemplary process for forming an intermediate electrode assembly in accordance with embodiments of the present invention.

As described in greater detail below, embodiments of the present invention may be implemented at various different stages of the manufacturing process. For ease of understanding, a typical manufacturing process is first described below with reference to FIGS. 3A and 3B, followed by more detailed descriptions of embodiments of the present invention. Specifically, FIG. 3A is a high level flowchart illustrating a process 300 forming a molded carrier member having one or more electrode contacts embedded therein. Because a carrier member having embedded electrode contacts may, in certain embodiments, be subject to further processing, the component formed in FIG. 3A may or may not be the finished electrode assembly. As such, for ease of reference herein, a molded carrier member with electrode contacts will be referred to herein as an intermediate electrode assembly. As shown in FIG. 3A, process 300 begins at block 302 where an array of electrode contacts, sometimes referred to herein as a contact array, is assembled. After formation of the array of electrode contacts, at block 304 a bridge is formed over the array for transfer of the array to a molding die. At block 306, a carrier member is molded about the array of contacts to form the intermediate electrode assembly.

As noted, FIG. 3A illustrates embodiments of the present invention in which a bridge is formed over the contact array to transfer the array to the molding die. It would be appreciated that in alternative embodiments, a bridge is not used. As such, in these alternative embodiments, step 304 may be omitted from process 300 and the array of contacts may be otherwise transferred to a molding die for use in step 306.

FIG. 3B is a detailed flowchart illustrating the process which may be performed to accomplish the operations of blocks 302, 304 and 306 of FIG. 3A. As noted, formation of an intermediate electrode assembly begins with the step 302 of assembling an array of electrode contacts. As shown at block 310, the electrode contacts are arranged in a linear array in a welding die. In specific embodiments, each of the contacts are aligned with, and longitudinally spaced from, one another to form a distally extending array of electrode contacts. Next, at block 312, each of the electrode contacts are connected to a conductive pathway, such as a wire. In the embodiments of FIG. 3B, each electrode contact is connected to its conductive pathway by threading an end of the pathway through a ring, and then crimping the ring to form a contact that has an approximate U-shape and which is attached to the end of the conductive pathway. The distal end of the conductive pathway is welded to the electrode contact. This process is repeated until all the electrode contacts have been connected to a conductive pathway, thereby forming the contact array.

FIG. 3B illustrates embodiments in which electrode contacts are initially separate from the conductive pathways. As noted, the separate electrode contacts and pathways are connected to one another at block 312. It would be appreciated that in alternative embodiments of the present invention, the conductive pathways may be integral with the electrode contacts. In certain such embodiments, the electrode contacts and conductive pathways may be formed from a single sheet of a biocompatible metal or metal alloy such as, for example, platinum.

As noted, process 300 continues at step 304 by forming a bridge over the contact array. To form the bridge, at block 314 a silicone adhesive is deposited or otherwise applied to the non-stimulating surface of each of the electrode contacts. At block 316 the silicone adhesive is allowed to cure. As would be appreciated, there are a number of methods for curing a silicone or silicone adhesive including, for example, allowing the adhesive to cure on its own, curing by placing the welding die into a heated oven, UV curing, etc. After the silicone adhesive is cured, a production stylet is attached at block 317, and silicone, such as Liquid Silicone Rubber (LSR), is injected into the welding die at block 318. At block 320, the silicone is allowed to cure, thereby forming the bridge and securing the stylet. Similar to the silicone adhesive, there are a number of methods for curing silicone. The selected curing method may depend on, for example, the type of silicone used.

Process 300 continues by molding a carrier member at block 306. To form the carrier member the bridged array of electrode contacts is removed from the welding die at block 322. At block 326, the array of electrode contacts and conductive pathways are placed in a curved molding die, and the die is closed by a cover. At block 328 a carrier member material, such silicone is injected into the molding die. In one exemplary application, a High Consistency Peroxide Cure (HCRP) silicone is injected into the molding die. At block 330, the silicone is allowed to cure by utilizing, for example, one of the methods noted above. The cured silicone forms a carrier member in which the electrode contacts and conductive pathways are disposed.

The embodiments of FIG. 3B illustrate the formation of a pre-curved electrode assembly, sometimes referred to as peri-modiolar electrode assembly. It would be appreciated that embodiments of the present invention are also applicable to non-perimodiolar electrode assemblies which do not adopt a curved configuration. For example, embodiments of the present invention may be utilized with a straight electrode assembly, a mid-scala assembly which assumes a mid-scala position during or following implantation, short electrode assembly, etc.

In specific embodiments in which a straight electrode assembly is formed, it may not be necessary to transfer the electrode contacts and conductive pathways to a molding die. In such embodiments, a carrier member material may be injected into the welding die and cured as described above.

Furthermore, the embodiments of FIG. 3B illustrate the formation of the electrode assembly having a lumen for use with a stylet to maintain the pre-curved electrode assembly in a straight configuration during implantation. As noted above, embodiments of the present invention may be utilized during formation of a straight electrode assembly. In such embodiments, the stylet is not necessary and steps relating to formation of the lumen may be omitted from FIG. 3B. Similarly, it would be appreciated that other techniques for maintaining a pre-curved electrode assembly in a straight configuration during insertion are known in the art. Embodiments of the present invention may be implemented with these various techniques and, as such, the stylet is not necessary.

As noted above, aspects of the present invention are generally directed to treating the surface of an electrode contact of an electrode assembly to increase the effective surface area of the electrode contact without increasing the geometric surface area of the electrode contact. As noted above, the effective surface area of an electrode contact is the surface area having the ability to deliver electrical stimulation signals to a recipient, while the geometric surface area is the planar outer dimensions of the surface, and does not include any fluctuations or changes in the surface.

In certain embodiments of the present invention, the effective surface area of an electrode contact is increased by treating the surface of the contact to remove contaminates from the surface. Contaminates disposed on the surface of an electrode contact surface may impede or prevent the delivery of electrical stimulation signals via the covered portions, thereby reducing the effective surface area of the electrode contacts. Such contaminates may result from the manufacturing process. Exemplary contaminates include, but are not limited to, overmolding residuals, masking materials, adhesives, wash residue remaining after washing cycles or acidic baths, airborne contaminates, or residue remaining from contact between the surface and other materials or chemicals such as lenium, clorofluorocarbons, such as Freon®, etc.

In certain circumstances, contaminates may be formed on the electrode contact surfaces during manufacturing processes of an electrically-stimulating device materials are applied to the surface of the electrode contacts, and these materials are subsequently removed.

For example, in certain circumstances electrode contacts are overmolded with a material, such as silicone. In other circumstances a masking or adhesive material may be applied to the electrode contacts and subsequently removed. The inventors determined that, the residual material remaining on the surface following removal affects the effective surface area of the contact. For example, an exemplary 1 mm spot analysis performed on the surface of a platinum electrode contact from which a layer of overmold was removed reveals surface concentrations of: 20.1% Oxygen, 52.3% Carbon, 21.0% Silicone, and 6.6% platinum. The unwanted residuals include the Oxygen, Carbon, and Silicone. It would be appreciated that these concentrations are exemplary and merely provided to demonstrate that, after removal of an overmold material from an electrode contact, the residual surface concentrations of the overmold material may be significant.

Current electrode contact designs are limited to a relatively large geometric contact surface area, relative to the dimensions of the cochlea. The relatively large geometric surface area results from the limitation that charge density must be kept below levels at which formation of electrochemical by-products may occur. For example, for conventional cochlear implant electrode contacts, the minimum geometric surface area of a contact is approximately 0.0707 $mm^2$. It would be appreciated that the acceptable geometric surface area of an electrode contact may depend on a number of factors, and estimates provided herein are merely illustrative. By removing residuals and other surface contaminates to increase the effective surface area of the contacts, the charge density of the electrode contact is decreased. This decrease in charge density may provide the ability to form smaller sized electrode contacts than previously possible.

Referring specifically to cochlear implants, smaller electrode contacts are desirable for a number of reasons. For example, smaller electrode contacts reduce trauma to the delicate cochlea structures during insertion and, once implanted, have less negative impact on the normal functioning of the ear relative to larger electrodes. Specifically, conventional electrodes, once implanted, occupy significant space in the cochlea, thereby restricting its normal function and resulting in reduction in, or loss of, residual hearing.

Furthermore, smaller cochlear implant electrode contacts have the advantage of a smaller stimulation area and thus more discrete stimulation. Also, smaller electrode contacts increase the ability to have more contacts to be placed within contact arrays. This may enable the stimulation of more discrete groups of auditory neurons and might provide finer discrimination of speech and sound features.

FIG. 4 is a flowchart illustrating a process 400 for forming an electrode assembly in which the surfaces of electrode contacts are treated to substantially remove contaminates from the surfaces. As shown, process 400 begins at block 300 where a carrier member having electrode contacts embedded therein, referred to as an intermediate electrode assembly, is formed. In the illustrative embodiment, the intermediate electrode assembly is formed in accordance with the process described above with reference to FIGS. 3A and 3B.

Figure 5A:
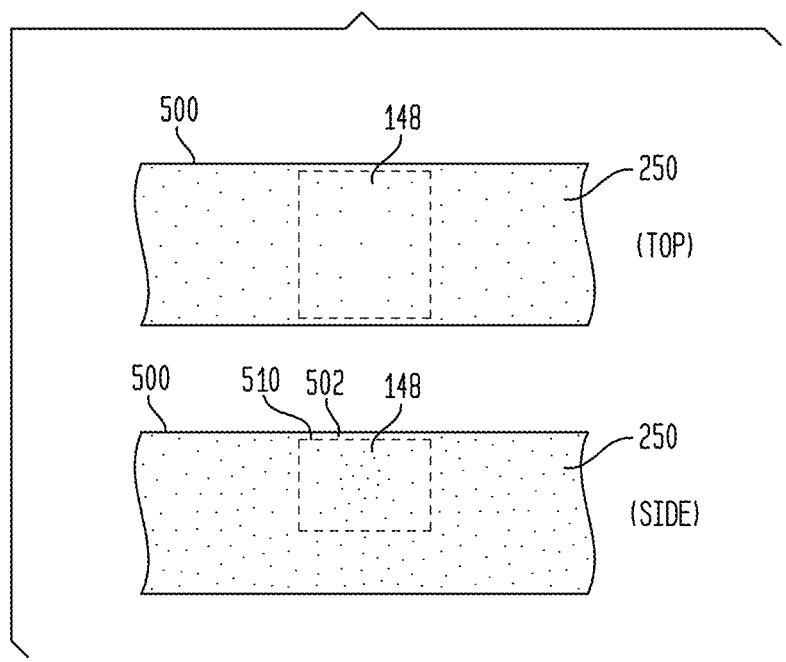
FIG. 5A illustrates a top and side view of a section of an electrode assembly during the process of FIG. 4, in accordance with embodiments of the present invention.

FIG. 5A illustrates a top and side view of a region of an intermediate electrode assembly 500 formed by the process of FIGS. 3A and 3B. The illustrated region of intermediate electrode assembly 500 comprises a silicone carrier member 250, as described above, and an electrode contact 148 embedded in the carrier member. As shown, a surface 510 of electrode contact 148 is covered by a thin layer of silicone 502.

Returning to FIG. 4, at block 402 a window is cut into the carrier member over the upper surfaces of the electrode contacts. At block 404, the carrier member material within the formed windows is removed. The removal of this section of the carrier member exposes the surfaces of the electrode contacts which, as noted above, may potentially have residual material remaining thereon.

Figure 5B:
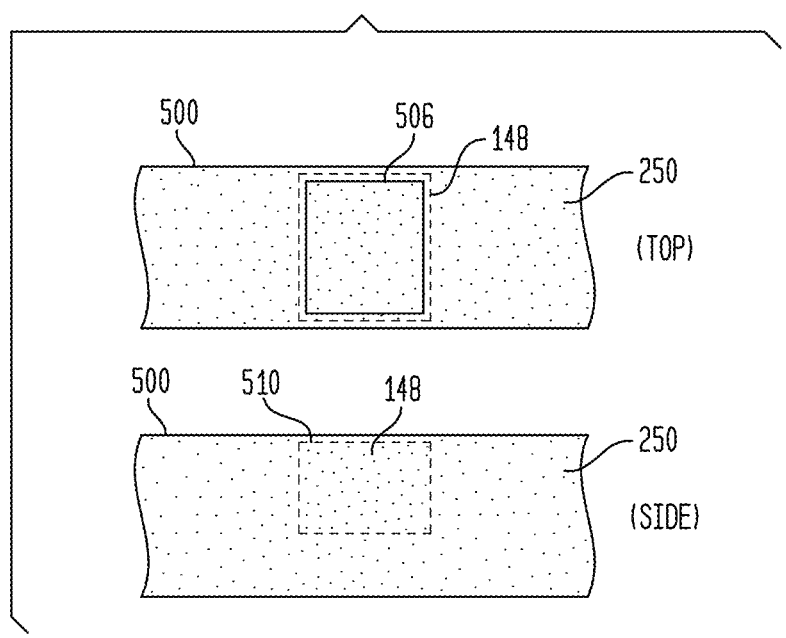
FIG. 5B illustrates a top and side view of a section of an electrode assembly during the process of FIG. 4, in accordance with embodiments of the present invention.
Figure 5C:
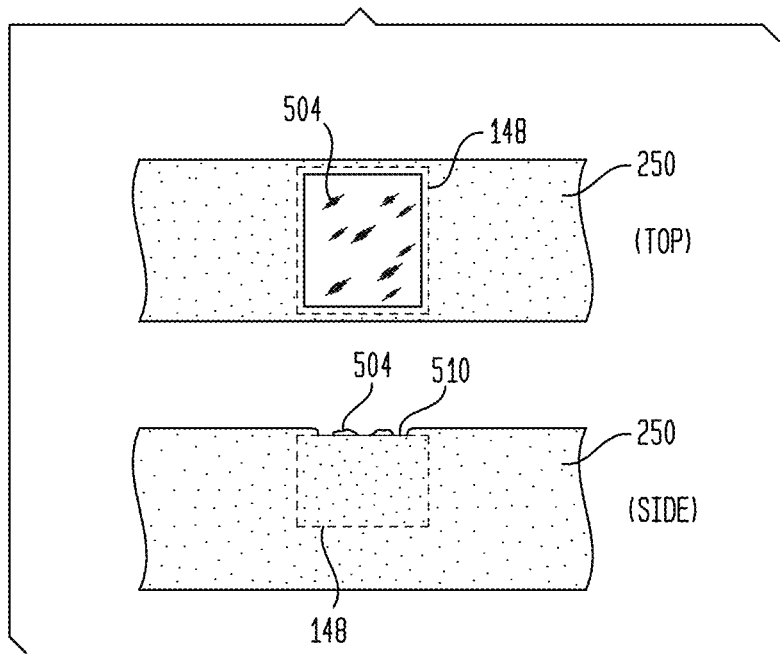
FIG. 5C illustrates a top and side view of a section of an electrode assembly during the process of FIG. 4, in accordance with embodiments of the present invention.

FIG. 5B illustrates the formation of a window 506 in intermediate electrode assembly 500. FIG. 5C illustrate the removal of windows 506 to expose surface 510 of electrode contact 148. As shown in FIG. 5C, exposed surface 510 has contaminates in the form of silicone residuals 504 thereon. For ease of understanding, silicone residuals 504 are schematically shown in FIG. 5C. However, in practice, silicone residuals 504 may be visible or invisible. In fact, as described in elsewhere herein, the inventors of the present application determined that previously undetected invisible residuals detrimentally reduce the effective surface area of electrode contacts following removal of the carrier member material. As such, embodiments of the present invention are effective in removing both visible and invisible silicone residuals or other contaminates.

As noted, FIGS. 4 and 5B-5C illustrate embodiments in which a window is cut into the carrier member for removal of the portion of the carrier member covering the electrode contacts. In alternative embodiments, it is not necessary to cut the windows into the carrier member. In such embodiments, the portion of the carrier member covering a contact is simply pulled away from the contact, and the carrier member breaks at the edges of the contacts. The carrier member breaks at the edges due to the thickness change which occurs in the carrier member. Specifically, the carrier member material is relatively thin over the electrode contacts, but becomes thick at the edges where the body of the carrier member is formed. In specific such embodiments the torn edges of the carrier member may be treated to form substantially straight edges.

Figure 5D:
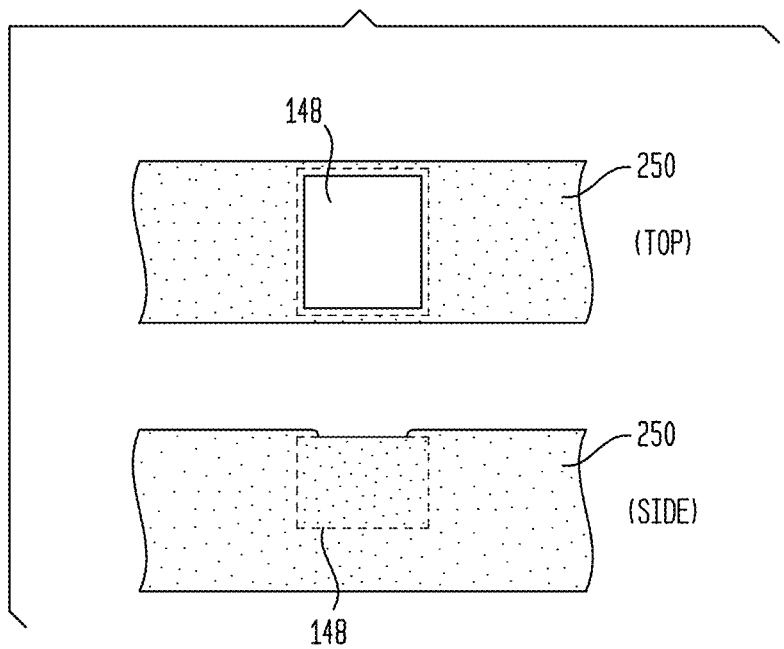
FIG. 5D illustrates a top and side view of a section of an electrode assembly during the process of FIG. 4, in accordance with embodiments of the present invention.

Returning again to FIG. 4, the exposed electrode contact surfaces are treated to remove the silicone residuals from the surfaces at block 406. FIG. 5D illustrates an exemplary region of a finished electrode assembly 118 illustrating electrode contact surface 510 free of the silicone residuals.

As noted, FIG. 4 illustrates the removal of the carrier member material at block 404, and the removal of residuals at block 406. It would be appreciated that steps of block 404 and 406 are distinct and separate processes performed sequentially and in different manners.

As detailed below, a number of processes may be utilized to remove contaminates from the surface of an electrode contact. FIG. 6 illustrates a first process of the present invention in which the surfaces 610 of electrode contacts 148 are treated via laser ablation. As used herein laser ablation refers to the deliver of a laser beam to the electrode surface. In the embodiments of FIG. 6, the laser beam is delivered at an intensity and/or for a duration which ablates contaminates on the contact surface.

As shown in FIG. 6, electrode assembly 118 is positioned on a working table 608. As noted above, electrode assembly 118 may be a pre-curved, straight, short, mid-scala and other types of electrode assembly. In embodiments in which electrode assembly 118 is pre-curved, the electrode assembly is straightened prior to laser ablation to provide easy access to electrode contacts 148. The electrode assembly may be straightened by inserting a stylet therein, or through the use of a straightening jig/sleeve. Electrode assembly may be secured to the table using, for example, vacuum, magnets, mechanical grips, dissolvable glue, etc.

In the embodiments of FIG. 6, a laser 602 is positioned above the working table, and is movable relative to electrode assembly 148. Laser 602 may be positioned so that a delivered beam 604 impacts electrode contact surfaces 610 at approximately a 90 degree angle to the surface. However, in other embodiments different angles may be used. It would be appreciated that laser beam 604 may be delivered to all or a portion of each electrode contact surface 610 to remove contaminates there from. That is, in specific embodiments, beam 604 may have a cross-sectional area which is smaller than that of surfaces 610 so that beam 604 only ablates a portion of surfaces 610 at any one time.

In one embodiment, laser 602 may comprise an excimer laser which generates an ultraviolet beam having a wavelength between approximately 150 and 250 nanometers (nm). For example, the excimer laser 602 may be a Krypton Fluoride (KrF) excimer laser which generates a laser beam having a wavelength of approximately 250 nm. In specific such embodiments, the laser beam has a wavelength of 248 nm. In other embodiments, laser 602 may comprise an Argon Fluoride (ArF) excimer laser which generates a laser beam having a wavelength of approximately 200 nm, and more specifically a beam of approximately 193 nm wavelength. A further description of a suitable 193 nm ArF excimer laser is provided in Fukami et al. "Ablation of Silicone Rubber Using UV-Nanosecond and IR-Femtosecond Lasers," Japanese Journal of Applied Physics, Vol. 53, No. 7A, pg. 4240-4241 (2004), the entire contents of which are hereby incorporated by reference.

In embodiments of the present invention, laser 602 may be operated with a pulse duration of between approximately 5 and 20 ns. In specific embodiments, a pulse of approximately 10 ns is applied.

Laser 602 may also comprise a pulsed laser which generates sequential pulses. In certain embodiments, the pulses may each have a duration of, for example, 130 femtoseconds (fs). The number of sequential pulses applied may be variable and based on, for example, a technician visually inspecting surfaced 610 after each pulse or a sequence of pulses. (or during the pulses) In other embodiments, the number, period, and time duration of each sequence of pulses may be fixed.

FIG. 6 illustrates embodiments in which laser 602 moves relative to electrode assembly 148. However, it would be appreciated that in alternative embodiments, electrode assembly 118 may be placed in a holder which moves relative to laser 602. The movement of the holder may be via an electro-mechanical system that is programmed to move the electrode assembly 118. This electro-mechanical system may be programmed to position each electrode contact 148 under the beam such that the electrode is impacted by a sequence of laser pulses as noted above. Once a region of an electrode contact surface 610 is sufficiently laser ablated, the electro-mechanical system may move the electrode assembly 118 so that a different region of the surface, or a different electrode contact 148, is impacted by the beam 604. The movements as well as the characteristic of the laser beam pulses (e.g., duration, number, etc.) may be programmed For example, in one embodiment, the characteristics of each sequence of pulses may be kept constant and the electrode assembly 118 moved so that each electrode is ablated a relatively uniform amount. In other embodiments, the movements and pulse sequences may be programmed to ablate different portions of each electrode contact differently.

Further, in embodiments of the present invention, a visual system may be used to log the position of electrode contacts 148 prior to starting the laser ablation process to help facilitate the positioning of the contacts during ablation. This visual system may obtain a visual image of electrode assembly 118 and map the location of electrode contacts 148. Using this map, electrode assembly 118 may be moved to ensure that electrode contacts 148 (or specific portions of the electrode contacts) are ablated. This visual system may be, for example, a 3-dimensional scanning system. In yet another embodiment, a real time imaging system may be used during ablation to help ensure proper location of beam 604 on electrode contacts 148. This real time imaging system may be used alone, or, for example, in conjunction with a visual system that maps the electrode contact locations prior to laser ablation.

It would be appreciated that not all surfaces 610 of electrode contacts 148 must be ablated. For example, in certain embodiments, only a subset of electrode contact surfaces 610 may be treated.

While FIG. 6 depicts an arrangement in which the electrode contacts 148 of the electrode assembly 118 undergo laser ablation, other surface modification techniques can be used instead and/or in addition to the laser ablation. Exemplary such techniques include, but are not limited to, electrical discharge machining (EDM), surface abrasion, electro-dissolution, chemical etching, acidic washing, etc.

In embodiments in which EDM is used, an EDM cutting system comprises an EDM cutting tool in the shape of surfaces 610 of electrode contacts 148. The EDM cutting tool 704 generates a series of electrical discharges between the EDM cutting tool and surface 610 of an electrode contact 148. The electrical discharges may be sufficient to vaporize the contaminants from the surface of the electrode contacts.

In embodiments in which surface abrasion is used, surfaces 610 are brought into contact with an abrasion tool having an abrasive member supported thereby. The abrasive member is moved across a surface 610 to remove contaminants from the surfaces of electrode contacts 148. The abrasive member may be, for example, a sharp instrument, or an abrasive material, such as, for example, diamond chips, sand (sandpaper), an abrasive stone, abrasive paste, etc.

In embodiments in which an acidic wash is used, electrode assembly 118 is placed in an acid bath such that the electrode contacts are exposed for a suitable period to a relatively dilute acid. Once done, the electrode contacts of electrode assembly 118 can be washed to remove any acidic residue. The time in which electrode assembly 118 is left in the acidic bath depends on the characteristics of the dilute acid, the material (e.g., silicone, urethane, etc.) used to form the electrode assembly, contaminates to be removed or other factors.

As noted, in further embodiments electro-dissolution and/or chemical etching may be used to remove contaminates from surfaces 610 of electrode contacts 148. Electro-dissolution refers to the dissolution of contaminate from surfaces 610 via electrolysis. Chemical etching refers to the process of using chemicals to dissolve contaminates from surfaces 610.

In still other embodiments, surfaces 610 may be treated through microblasting. As used herein, microblasting refers to the delivery of liquid CO2, sodium bicarbonate or other material to surfaces 610 to remove contaminates.

In the embodiments of the present invention, two or more of the above methods may be implemented to remove contaminates from surfaces 610. For example, in one embodiment, surfaces 610 may first be treated using laser ablation, and then a second step (or third step), such as microblasting, may be performed to further clean the electrode surfaces.

Furthermore, the techniques described above may further be followed by an additional step in which surfaces 610 are cleaned to, for example, remove chemical residues resulting from the surface treatment.

FIGS. 4-6 illustrate embodiments of the present invention in which contaminates are removed after the molding process. It would be appreciated that contaminates may be removed at different times during the manufacturing process including any time where a contaminate is potentially formed on contact surface such as: during masking, application of adhesives, following washing cycles or acidic baths, or any time when the surfaces are exposed to airborne contaminates, or are placed in contact with chemicals such as lenium, clorofluorocarbons, such as Freon®, etc., or other undesirable materials.

As noted, the above aspects of the present invention are directed to increasing the effective surface area of an electrode contact without increasing the geometric surface area of the contact by removing contaminates from the contact surface. In further embodiments of the present invention, the effective surface area of an electrode contact is increased by contouring the contact surface. That is, the contact surface is treated to form a pattern of indentations into the surface. By contouring the contact surface, the effective surface area of the electrode contact is increased without increasing the geometric surface area of the contact.

FIG. 7 is a flowchart illustrating an exemplary process 700 for forming an electrode assembly having contoured electrode contact surfaces in accordance with exemplary embodiments of the present invention. As shown, process 700 begins at block 300 where an intermediate electrode assembly comprising a carrier member supporting electrode contacts is formed. In the illustrative embodiments, the intermediate electrode assembly is formed using the embodiments described above with reference to FIGS. 3A and 3B. However, as described above, a number of different methods may be implemented to form the intermediate electrode assembly.

At block 702, a window is cut into the carrier member over the upper surfaces of the electrode contacts. At block 704, the carrier member material within the formed windows is removed. The removal of this section of the carrier member exposes the surfaces of the electrode contacts. As described in greater detail below, after exposing the surfaces of the electrode contacts, the surfaces are contoured. Specifically, conventional electrode contacts have a generally planar and substantially smooth surface. Embodiments of the present invention generate a plurality of indentations in one or more regions of the substantially smooth surface, thereby providing the surface with a desired degree of roughness. FIGS. 12A-12D schematically illustrate different patterns of indentations, while FIGS. 8A-10B illustrate different exemplary contours that may be formed in embodiments of the present invention.

Figure 8A:
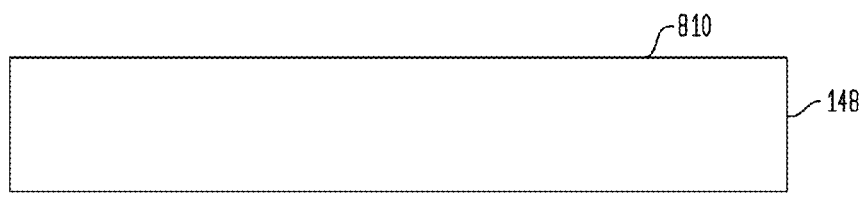
FIG. 8A is a schematic side view of an electrode contact having an untreated surface.
Figure 8B:
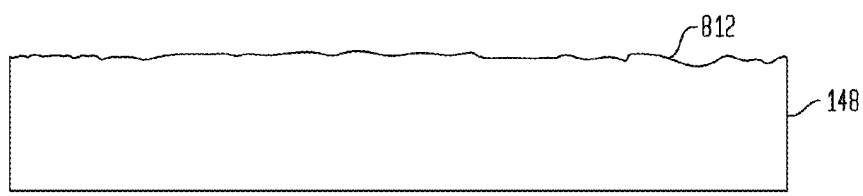
FIG. 8B is a schematic side view of an electrode contact having a contoured surface in accordance with embodiments of the present invention.
Figure 8C:
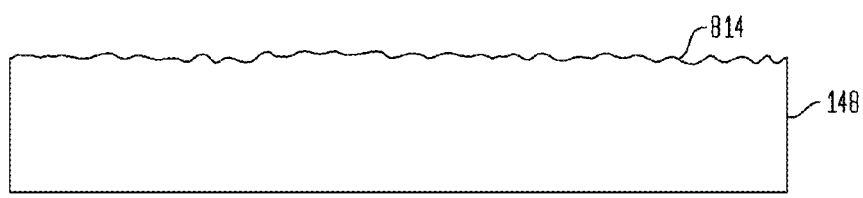
FIG. 8C is a schematic side view of an electrode contact having a contoured surface in accordance with embodiments of the present invention.
Figure 8D:
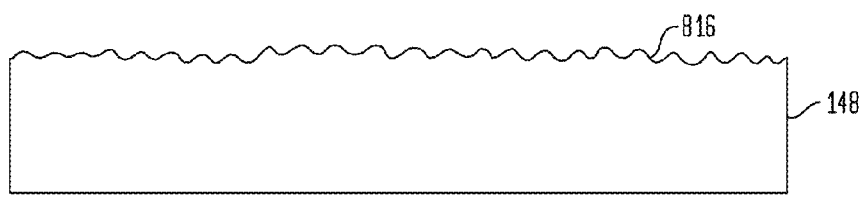
FIG. 8D is a schematic side view of an electrode contact having a contoured surface in accordance with embodiments of the present invention.

FIGS. 8A-8D are side views of an electrode contact 148 having different contoured surfaces in accordance with embodiments of the present invention. FIG. 8A illustrates an electrode contact 148 electrode having a generally planar, substantially smooth surface 810. FIGS. 8B-8D illustrates surfaces 812, 814 and 816, respectively, each having a different contour and degree of roughness. As shown, the roughness of the surfaces increases from FIG. 8B to FIG. 8D. In these embodiments, the depth of the indentations increases from FIG. 8B to FIG. 8D, thereby increasing the roughness.

As shown, surfaces 812, 814 and 816 include indentations such that, when moving across the surface of the electrode contact, the distance traveled is greater for each of surfaces 812, 814, and 816 than for smooth surface 810. Thus, the effective length and width of the surfaces 812, 814 and 816 is greater than the effective length and width of smooth surface 810. Therefore, when taking into account all 3-dimensions, the effective surface area of a surface treated electrode contact will be greater than the effective surface area of a smooth electrode contact. It would be appreciated that the embodiments of FIGS. 8A-8D are provided solely to illustrate the concept of how a treated surface may increase the effective surface area of an electrode contact. The illustrated contours are schematic and are not shown to scale.

Figure 9A:
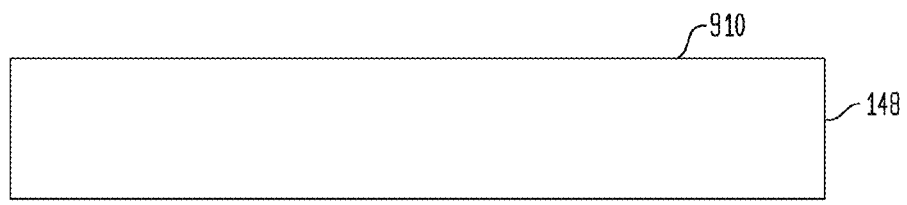
FIG. 9A is a schematic side view of an electrode contact having an untreated surface.
Figure 9B:
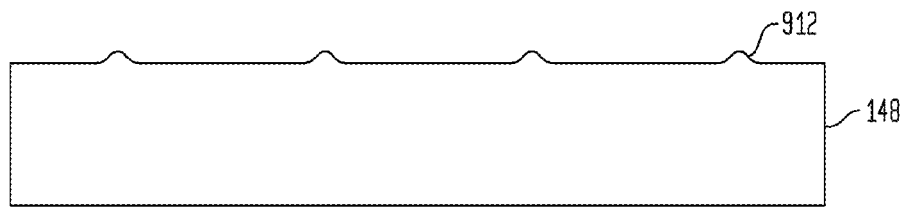
FIG. 9B is a schematic side view of an electrode contact having a contoured surface in accordance with embodiments of the present invention.
Figure 9C:
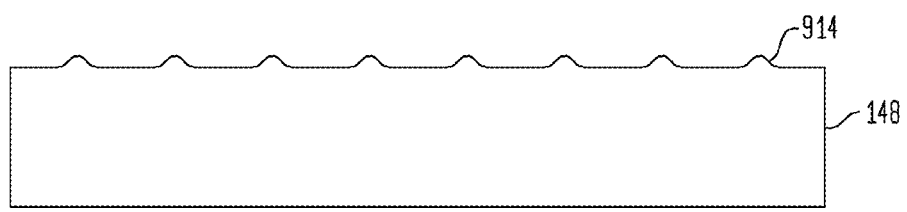
FIG. 9C is a schematic side view of an electrode contact having a contoured surface in accordance with embodiments of the present invention.
Figure 9D:
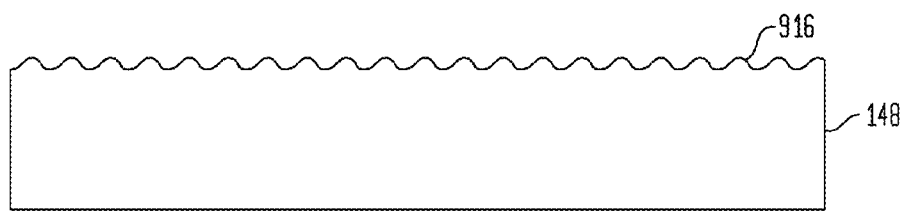
FIG. 9D is a schematic side view of an electrode contact having a contoured surface in accordance with embodiments of the present invention.

FIGS. 9A-9D are side views of an electrode contact 148 having different contoured surfaces in accordance with embodiments of the present invention. FIG. 9A illustrates an electrode contact 148 having a generally planar, substantially smooth surface 910. FIGS. 9B-9D illustrates surfaces 912, 914 and 916, respectively, each having a different contour and different degree of roughness. As shown, the roughness of the surfaces increases from FIG. 9B to FIG. 9D. In these embodiments, the density of the indentations increases from FIG. 9B to FIG. 9D, thereby increasing the roughness.

There are a number of techniques which may be used in embodiments of the present invention to contour the surface of electrode contact surfaces to increase the effective surface area. One exemplary method uses laser ablation. A suitable arrangement for contouring a contact surface via laser ablation was previously described as with reference to FIG. 6. However, in contrast to laser 602 of FIG. 6 which delivers a beam at an intensity and a duration that ablates contaminates on the surface of the electrode contact. For example, excimer lasers having wavelengths between approximately 250 nm and approximately 150 nm, and more specifically lasers having wavelengths between 248 nm and 157 nm may be used. In certain embodiments, the ablation process may be controlled by altering the intensity of the laser and/or varying the time length of the pulses.

Figure 10A:
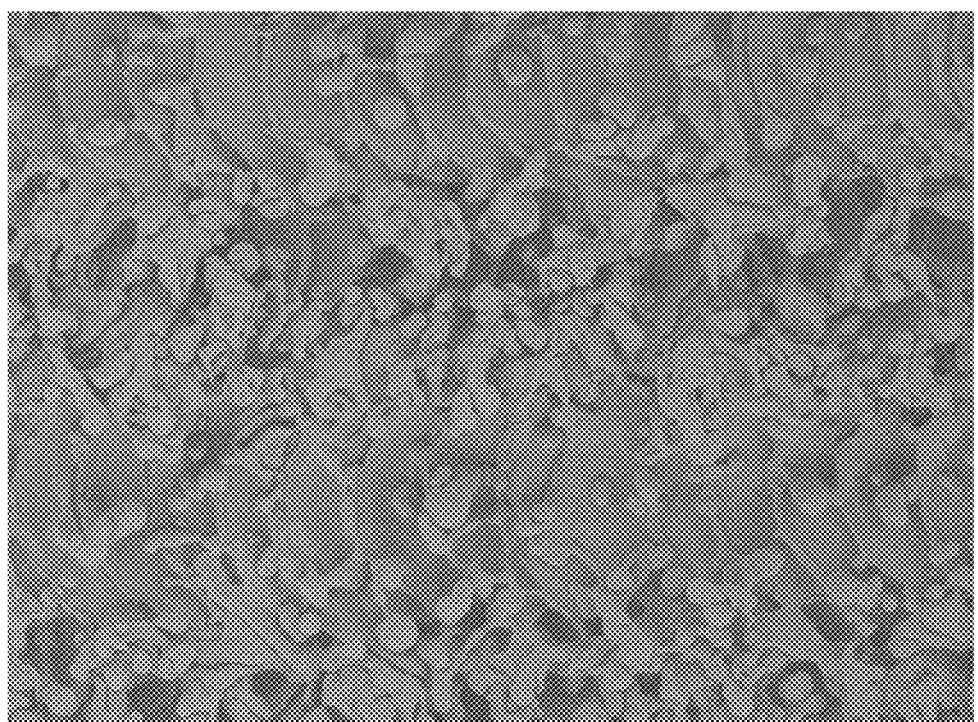
FIG. 10A is an image of an electrode contact surface in which the surface has been contoured through laser ablation.
Figure 10B:
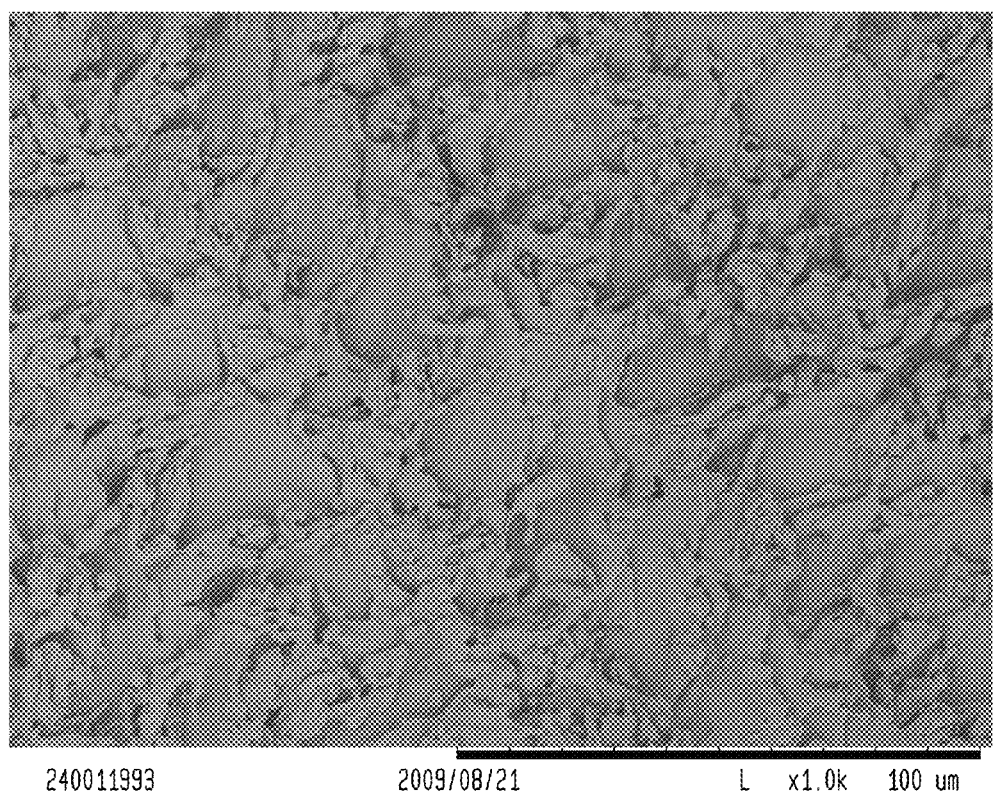
FIG. 10B is an image of an electrode contact surface in which the surface has been contoured through laser ablation.

FIGS. 10A and 10B are images of portions of two electrode contact surfaces treated via laser ablation to increase the surface area of the electrode contacts. Specifically, FIG. 10A illustrates an exemplary platinum contact surface treated with a 20 W Fiber Laser having a frequency of 40,000 Hz for approximately 11.4 seconds at a power of 0.9%. FIG. 10B illustrates a platinum surface treated such that the surface area is greater than that shown in FIG. 10A. That is, the surface shown in FIG. 10B is rougher than that shown in FIG. 10A. In the embodiments of FIG. 10B, the surface is treated with a 20 W Fiber Laser having a frequency of 20,000 Hz for approximately 15.2 seconds at a power of 0.9%.

As noted above, a number of other techniques may be implemented to contour an electrode contact surface to increase the effective surface area thereof One such technique is referred to as a Hi-Q process, while another technique is a Nano-porous process. An exemplary Hi-Q process electrochemically roughens the surface of a platinum electrode. A surface treated using a Hi-Q process, when viewed under a scanning electron microscope, consists of long columns of platinum. Each column may be hundreds of nanometers in diameter and form the bulk of the surface. In certain embodiments, a Hi-Q processed electrode contact, sometimes referred to as a HiQ electrode contact, may have an effective surface area which is 50-200 times greater than the geometrical area of the contact.

As noted above, the size of electrode contacts may be limited because the charge per unit area that the electrode holds must be lower than a level that cause harmful electrochemical reactions with the recipient's tissue. Because the effective surface area of a HiQ electrode contact is much larger than a conventional electrode, the HiQ electrode has the ability to transfer 50-200 times as much charge into tissue without causing the noted dangerous electrochemical by-products. As such, electrodes having relatively small geometric areas can be used safely because the effective surface area resulting from the Hi-Q process remains relatively large.

A further technique which may be implemented includes treating the electrode contact surfaces with a punch. In such embodiments, a punch may incorporate a stamp which marks the surface area of the contact with plurality of indentations. In still other embodiments, electrical discharge machining (EDM), electro-dissolution, chemical etching, etc. may be used to form the indentations into the electrode contact surfaces.

In other embodiments, gel based electrochemistry may be used to form indentations in the electrode contact surfaces. In these embodiments, a solution containing desired species used to erode material is loaded with a high percentage of non-ionic surfactants which manifest as a gel-like material. The gel-like material is deposited using, for example, a syringe with an appropriate dispensing system, onto the electrode contacts. The electrochemical process then takes place in the areas where the gel-like material is deposited to form the indentations. Once the process is completed, the gel-like structure is washed from the electrode contacts exposed formed indentations. In certain embodiments the gel-like material is dissolvable in water.

In another embodiment, radio frequency power may be utilized to form indentations in the electrode contacts. An exemplary method for forming indentations using radio frequency power is described in U.S. Pat. No. 5,118,400, the content of which is hereby incorporated by reference herein.

As noted above, current electrode contact designs are limited to a relatively large geometric surface area resulting from the limitation that charge density must be kept below levels at which formation of electrochemical by-products may occur. By contouring the surfaces of the electrode contacts as described above to increase the effective surface area, the charge density on the modified electrode contacts is decreased. Similarly, the overall impedance of the electrode contact for a given geometric surface area may be reduced. These advantages facilitate the use of smaller electrode contacts for a given current intensity, we well as make the system more efficient because less energy is required at the electrode-tissue interface relative to conventional electrode contacts.

Figure 12A:
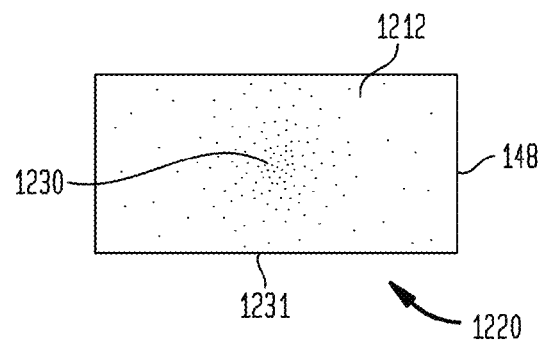
FIG. 12A is a schematic top view of an electrode contact surface in which the surface has been contoured in accordance with embodiments of the present invention.
Figure 12B:
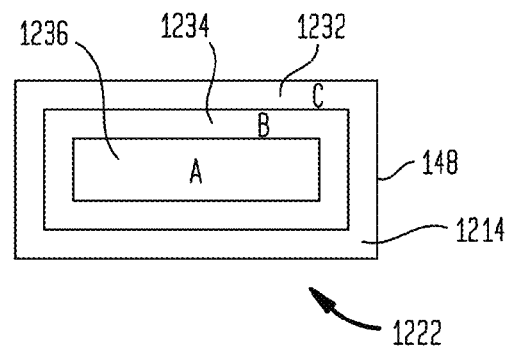
FIG. 12B is a schematic top view of an electrode contact surface in which the surface has been contoured in accordance with embodiments of the present invention.

An electrode contact in accordance with embodiments of the present invention may be contoured in a number of different manners to increase the effective surface area. In certain embodiments of the present invention, the electrode contact surfaces are contoured such that the center of the surface has the lowest impedance (i.e. highest conductance). This is accomplished by providing the center of the surface with the largest effective surface area per area unit (i.e. per mm$^2$, cm$^2$, etc.) relative to the other regions of the surface. As described below, FIGS. 12A-12B illustrate various such contour patterns which may be implemented in embodiments of the present invention.

Figure 11:
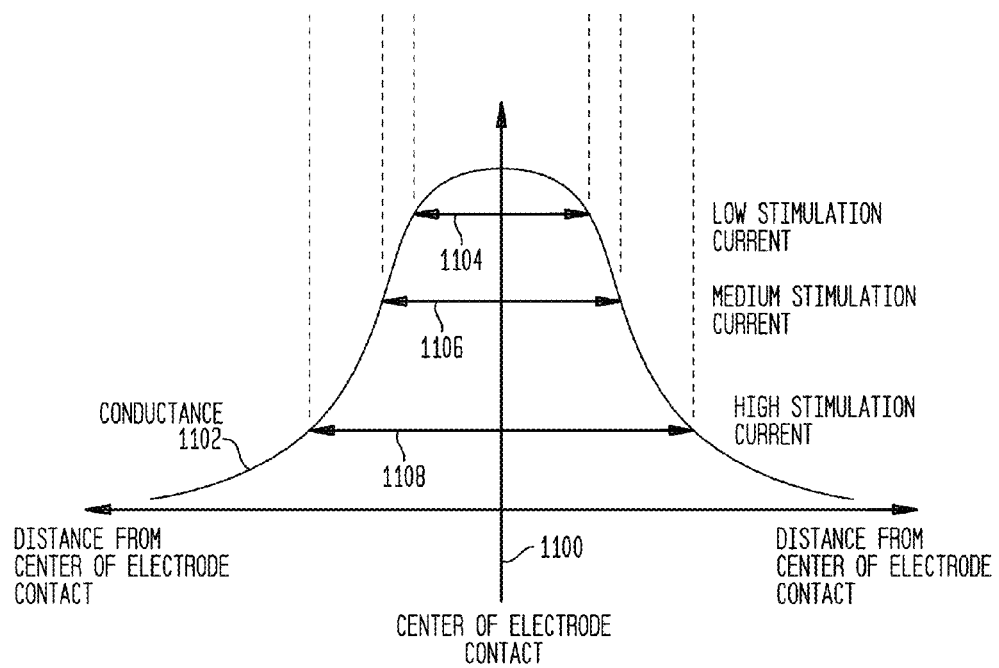
FIG. 11 is a schematic diagram illustrating the spread of stimulation signals in relation to current levels, in accordance with embodiments of the present invention.

In embodiments in which the impedance of the electrode contact is lowest at the center of the surface, the delivered current will be primarily focused through the center of the surface. The inventors of the present invention further theorize that focusing the current primarily through the center of the electrode contact may provide more frequency specificity in stimulation of the tonotopically organized cochlea. FIG. 11 is a schematic diagram of electrode contact conductance versus distance from the center of an electrode illustrating this theory.

In FIG. 11, the center of the electrode contact is represented by axis 1100, and the conductance is represented by curve 1102. As shown, the electrode contact has reduced impedance (Z) and higher conductance 1102 (1/Z) at center of the electrode contact 1100. By selecting varying levels of stimulation current it may be possible to more precisely control the spread of the current, and thus the area of nerve cells which are stimulated above the critical threshold to evoke a percept.

More specifically, by applying a sufficiently low stimulation current, an area of cells represented by arrow 1104 will be stimulated with a current above the critical threshold. By applying a sufficiently high stimulation current, a relatively larger number of nerve cells, represented by arrow 1108, will be stimulated. Furthermore, by applying a stimulation current between the high and low levels, referred to herein as medium stimulation current, a number of cells represented by arrow 1106 will be stimulated above threshold. Therefore, by varying the level of current delivered via the contact, the area of stimulated cells may be varied with significantly greater specificity than is possible with conventional electrode contacts. Also, this increased specificity is accomplished in a manner which does not result in excessive and potentially tissue-damaging current density at the edges of the electrode contact (i.e. as is the problem with conventional small electrode contacts). The area of cells which may be stimulated by each current level may depend on the stimulation current and on the impedance characteristic of the electrode contact.

As noted, graph of FIG. 11 illustrates that the spread of current from a treated contact in accordance with embodiments of the present invention. An exemplary curve for a conventional un-treated contact of the same size would not be as narrow and the center point of the curve would be lower. Thus the treated contact provides more focused current delivery as compared to conventional contacts.

As noted above, FIGS. 12A-12D schematically illustrate various contour patterns which may be formed in electrode contacts of the present invention. The electrode contacts of FIGS. 12A-12D are schematically shown as planar rectangular surfaces. It would be appreciated that this shape was selected for ease of illustration and does not limit the shape of electrode contacts which may be implemented in accordance with embodiments of the present invention.

FIG. 12A illustrates a pattern in which the roughness, and hence the effective surface area per area unit, of an electrode contact 148 gradually decreases outwardly from the center 1230 of the electrode contact surface. That is, the surface 1212 of electrode contact 148 has the highest effective surface area per area unit at center 1230, and the lowest effective surface area per area unit towards edges 1231. The pattern illustrated in FIG. 12A is referred to as graduated pattern 1220. As described above, graduated pattern 1220 results in the focusing of current delivered electrode contact 148 primarily through center 1230.

FIG. 12B illustrates another embodiment of the present invention in which a stepped contour pattern 1222 is implemented. As shown, surface 1214 of electrode contact 148 has three regions 1236, 1234 and 1232 each with a different roughness, and hence different effective surface areas per unit. Region 1236 has an effective surface area per unit (A) which is the highest, while region 1232 has an effective surface area per unit (C) which is the lowest. The effective surface area per unit (B) of region 1234 is between that of regions 1236 and 1232. As described above, stepped pattern 1222 results in the focusing of current delivered electrode contact 148 primarily through region 1236, and spreading outwards there depending on, for example, the impedance of each region 1236, 1234 and 1232.

FIG. 12B illustrates embodiments in which the stepped regions have a rectangular pattern. It would be appreciated that other step patterns are within the scope of the present invention including square shapes with rounded corners, circular shapes, or other shapes. In other embodiments, each region may have a unique shape. As would be appreciated, the use of square, circular, oval, etc. to describe the shape of a contoured area refers to the outer shape of the area. Further, it should be noted that the electrode contact surfaces may include any number of regions having different effective surface areas per area unit.

Figure 12C:
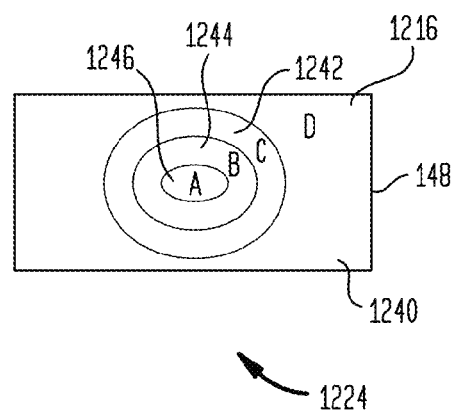
FIG. 12C is a schematic top view of an electrode contact surface in which the surface has been contoured in accordance with embodiments of the present invention.

FIG. 12C illustrates one alternative stepped pattern 1224 formed in the surface 1214 of electrode contact 148. As shown, surface 1216 has four regions 1246, 1244 and 1242 and 1240 each with a different roughness, and hence different effective surface areas per unit. Regions 1246, 1244 and 1242 each have a circular shape rather than the rectangular shape of FIG. 12B.

Region 1246 has an effective surface area per unit (A) which is the highest, while region 1240 has an effective surface area per unit (D) which is the lowest. The effective surface area per unit (B) of region 1244 and (C) of region 1242 are between that of regions 1246 and 1240, with the effective surface areas per unit (B) being larger than (C). As described above, stepped pattern 1224 results in the focusing of current delivered electrode contact 148 primarily through region 1236, and spreading outwards there depending on, for example, the impedance of each region 1236, 1234 and 1232.

Figure 12D:
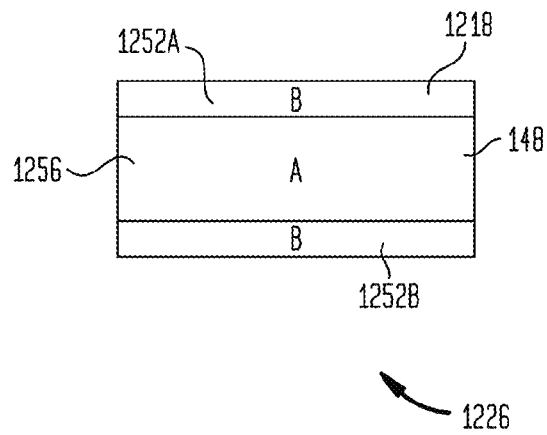
FIG. 12D is a schematic top view of an electrode contact surface in which the surface has been contoured in accordance with embodiments of the present invention.

FIG. 12D illustrates a still further pattern 1226 in which surface 1218 of electrode contact 148. In these embodiments, surface has a first region 1256 extending the width of the electrode. Region 1256 has an effective surface area per unit (A). Bordering opposing sides of region 1256 are regions 1252 each having an effective surface area per unit (B). Effective surface area per unit (B) is smaller than (A) such that current delivered via electrode contact 148 is primarily focused through region 1256.

FIG. 12D illustrates embodiments in which region 1256 is centered across the length of the electrode contact. It would be appreciated that in alternative embodiments, region 1256 may be extend across the width of contact 148. In such embodiments, region 1256 is referred to as centered across the width of contact 148. It would be further appreciated that left or right cochlea specific electrodes may be designed by having a roughened region disposed at different areas of the surface, and not necessarily at the center.

It would be appreciated that patterns of FIGS. 12A-12D are merely illustrative and do not limit the present invention. It would also be appreciated that the techniques described above may be utilized to form the patterns of FIGS. 12A-12D.

Figure 13A:
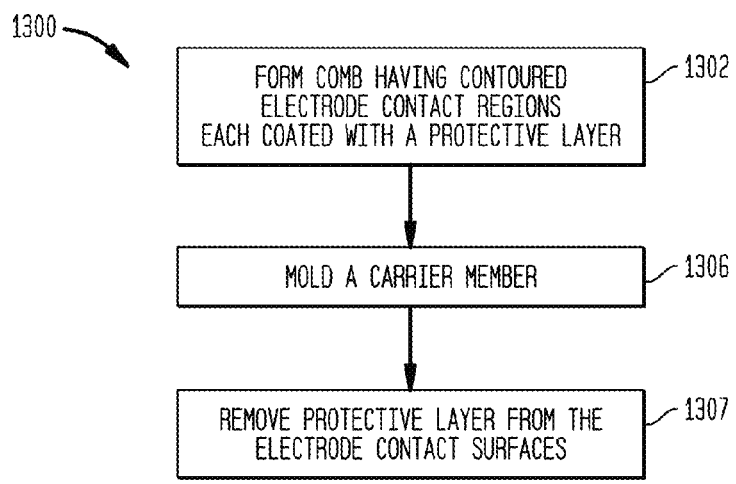
FIG. 13A is a flowchart illustrating a method for forming an electrode assembly having contoured electrode contact surfaces, in accordance with embodiments of the present invention.

As noted above, electrode contact surfaces may be contoured after molding of an electrode assembly carrier member. In other embodiments of the present invention, electrode contact surfaces may be contoured at other stages of the manufacturing process. FIG. 13A is a high level flowchart illustrating one exemplary process 1300 in which the electrode contact surfaces are contoured during formation of an array of contacts.

As shown, process 1300 begins at 1302 where a comb having contoured electrode contact regions each coated with a protective material is formed. As described in International Patent Application No. PCT/US2008/083794; filed Nov. 17, 2008, entitled "ELECTRODE ARRAY AND METHOD," a comb is a unitary piece comprising a plurality of electrode contacts extending from a spine. An exemplary comb formed via the process of block 1302 is described further below with reference to FIGS. 14A and 14B. Further details of an exemplary process 1302 are provided below with reference to FIG. 13B.

At block 1306, the carrier member is formed and molded, as described above, into a pre-curved, straight, etc., electrode assembly. Process 1300 further includes process 1307 in which the protective layer of material is removed from each of the electrode contact surfaces. Specifically, after the process of block 1306, the portions of carrier member material covering the electrode contact surfaces is removed. During removal of the carrier member material, the protective layer formed on the surfaces during step 1302 is also removed to provide the stimulating contact surface. In specific embodiments of FIG. 13A, a laser is used in step 1306 to cut around the electrode contacts and the carrier member layer covering the contacts is removed together with the protective layer underneath and adjacent the electrode contact surface.

Figure 13B:
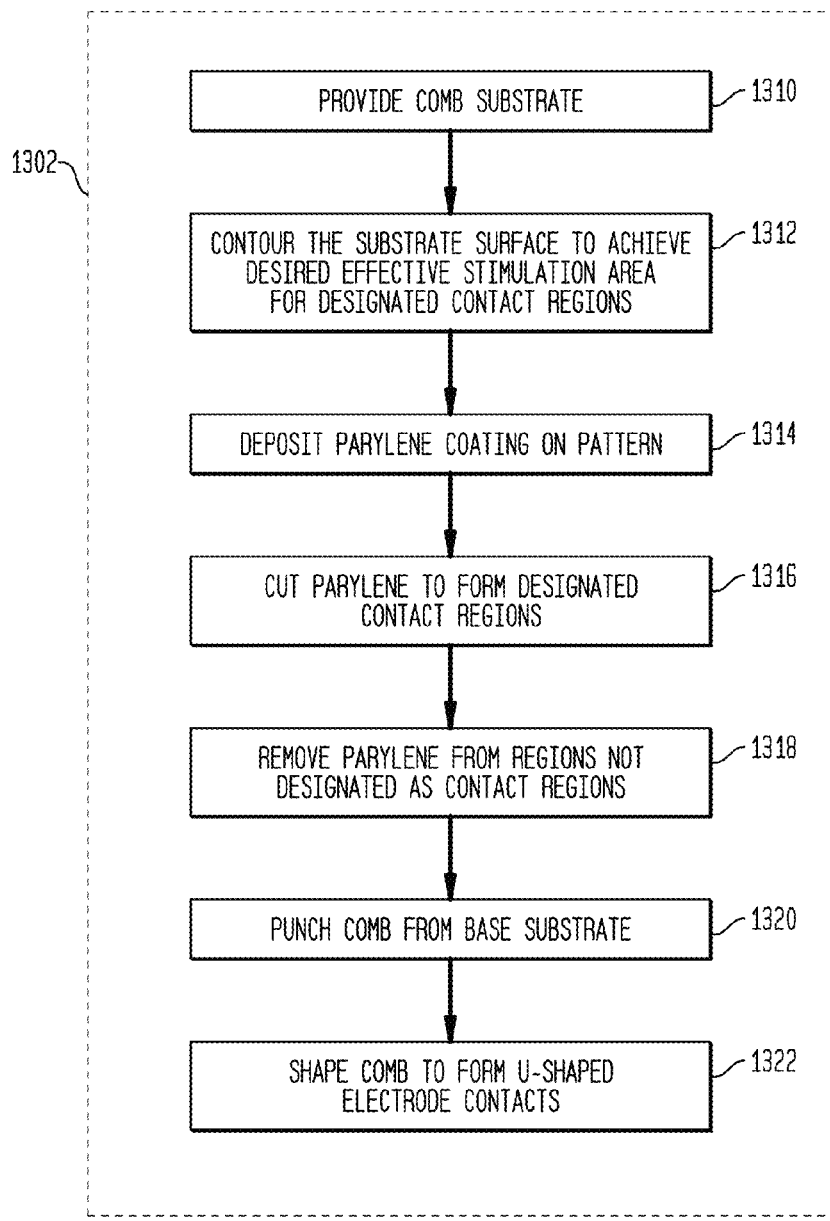
FIG. 13B is a flowchart illustrating a method for forming a comb having surface treated electrode contacts.
Figure 14A:
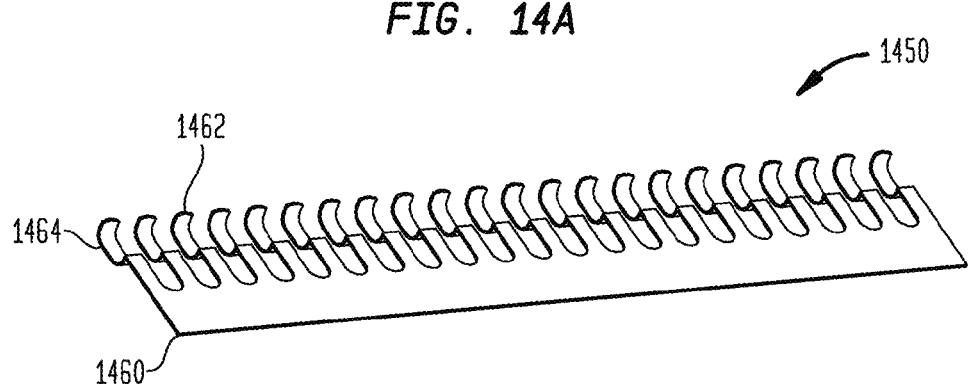
FIG. 14A is a perspective view of a comb formed via the method of FIG. 13B.
Figure 14B:
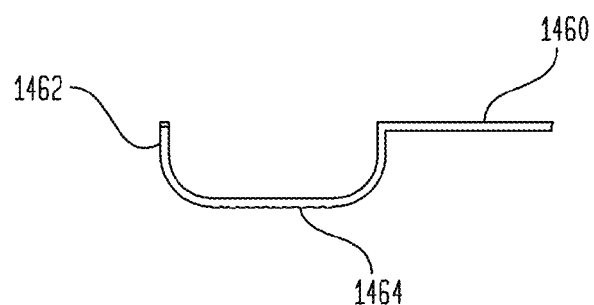
FIG. 14B is side view of the comb of FIG. 14A.

As noted, FIG. 13B is a detailed flowchart illustrating one exemplary process 1302 of FIG. 13A in greater detail. Process 1302 begins at block 1310 where a biocompatible base substrate is provided. In certain embodiments, the provided substrate is a platinum strip.

At block 1312, a surface of the platinum strip is contoured with patterns of indentations as described above with reference to FIGS. 8A-12D. Specifically, regions of the platinum strip are treated so that electrode contacts have patterns of increased effective stimulation area formed therein. These contoured regions are referred to herein as designated electrode contact regions.

At block 1314, a protective layer is formed on the platinum strip and is allowed to cure. As shown, the embodiments of FIG. 13B illustrate the use of one specific type of protective coating, namely parylene. However, it would be appreciated that other types of protective coating may also be used.

At block 1316, the parylene layer is cut around the designated contact regions, and at block 1318 the parylene which does not cover the designated electrode contact regions is removed. As such, the parylene forms a protective layer on the regions designated as contacts.

At block 1320, the comb comprising the spine and integrated electrode contacts is punched from the base substrate. At block 1322 the comb is shaped to form U-shaped electrode contacts. This comb having the shaped electrode contacts is then used in step 1304 of FIG. 13A to assemble the contact array.

As noted above, FIGS. 14A and 14B are perspective and end views, respectively, of a comb 1450 formed through the process of FIG. 13B. As shown, comb 1450 comprises spine 1460 and a plurality of electrode contacts 1462 extending there from. As noted, the surface 1464 of electrode contacts 1462 is treated as described above to increase the effective surface area thereof For ease of illustration, the parylene layer covering surfaces 1464 has been omitted.

Figure 14C:
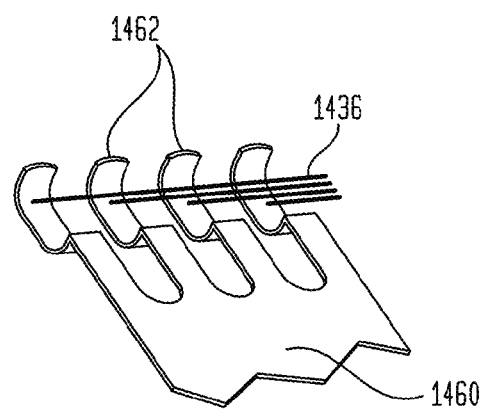
FIG. 14C is a perspective view of the comb of FIG. 14A having conductive pathways attached thereto, in accordance with embodiments of the present invention.

As noted, after formation of comb 1450, the electrode contacts 1462 are connected to conductive pathways 1436. This arrangement is shown in FIG. 14C.

FIGS. 13A and 13B illustrate a specific method which may be implemented in embodiments of the present invention. It would be appreciated that these embodiments are merely illustrative and other embodiments may also be implemented. For example, in one alternative embodiment during formation of the comb, a dissolvable protective layer of material may be applied to the surfaces of the designated electrode contact regions. This layer may then be dissolved after molding and cutting of the carrier to remove material covering the surfaces of the electrode contacts. In other embodiments, a comb is not utilized and the electrode assembly is formed using, for example, the methods described above with FIGS. 3A and 3B. In one such example, the dissolvable layer of material may be a Polyvinyl Alcohol (PVA) layer. It would also be appreciated that the order of the steps shown in FIGS. 13A and 13B are merely illustrative and may change.

It would also be appreciated that further alternatives are applicable to the embodiments of FIGS. 13A-13B. For example, in one alternative all or a large portion of the comb may be treated with a pattern which encourages adhesion of the carrier member thereto. This may also be combined with plasma activation to further increase adhesion.

As noted, embodiments of the present invention have been described with reference to various types of surface treatment to remove contaminates and/or to physically modify the surface of electrode contacts. It would be appreciated that the various embodiments of the present invention may be used alone or in combination with one another.

Further features and advantages of the present invention are described in commonly owned and co-pending U.S. Utility Patent Application entitled "CONTOURED ELECTRODE CONTACT SURFACES," filed Dec. 1, 2009; U.S. Utility Patent Application entitled "ELECTRODE CONTACT CONTAMINATE REMOVAL," filed Dec. 1, 2009; U.S. Utility patent application Ser. No. 11/159,256, entitled "METHODS FOR MAINTAINING LOW IMPEDANCE ELECTRODES," filed Jun. 23, 2005; and U.S. Utility patent application Ser. No. 12/423,562, entitled "MAINTAINING LOW IMPEDANCE OF ELECTRODES," filed Apr. 14, 2009. The content of these applications are hereby incorporated by reference herein.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All patents and publications discussed herein are incorporated in their entirety by reference thereto.

What is claimed is:

1. A method for manufacturing an electrode assembly, the method comprising:
    contouring the surface of at least one electrode contact, so as to increase an effective surface area of the electrode contact surface without increasing the geometric surface area of the electrode contact comprising contouring a biocompatible substrate to form at least one designated electrode contact area having indentations formed therein;
    depositing a protective coating on the contoured surface;
    molding a carrier member about the at least one electrode contact, wherein the surface of the at least one electrode contact is covered by a layer of the carrier member material;
    cutting the coating around each designated electrode contact area; and
    removing the protective coating and the layer of carrier member material from the surface of the at least one electrode contact, comprising removing the coating from the regions of the substrate outside each designated electrode contact area.

2. The method of claim 1, further comprising:
    punching a comb from the substrate, the comb comprising at least one comb tooth comprising a designated electrode contact area; and
    shaping the comb to form at least one u-shaped electrode contact, each u-shaped electrode contact comprising one at least one designated electrode contact area.

3. The method of claim 1:
    wherein the depositing comprises depositing a dissolvable layer of material on the contoured substrate.

4. The method of claim 3, further comprising:
    punching a comb from the substrate, the comb comprising at least one comb tooth comprising a designated electrode contact area; and
    shaping the comb to form at least one u-shaped electrode contact, each u-shaped electrode contact comprising one at least one contoured designated electrode contact area.

5. The method of claim 1, wherein depositing a protective coating on the contoured surface comprises:
    depositing a parylene layer on the contoured surface.

6. The method of claim 1, wherein contouring comprises:
    contouring the surface of at least one electrode contact such that the effective surface area per area unit of a center region of the at least one electrode contact is larger than the effective surface area per area unit of the of the region of the surface outside the center region.

7. The method of claim 6, wherein contouring the surface comprises:
    forming a pattern of indentations such that the effective surface area per area unit of a region of the surface outside the center region decreases from the center region towards edges of the at least one electrode contact.

8. The method of claim 6, wherein contouring the surface comprises:
    modifying one or more portions of the surface outside of the center region such that each portion has a different effective surface area per area unit, wherein the portion adjacent the center region has a greater effective surface area per area unit than any other of the one or more portions.

9. The method of claim 1, wherein contouring the surface of the at least one electrode contact comprises:
    laser ablating the surface of at least one electrode contact.

10. The method of claim 9, wherein laser ablating the surface of the at least one electrode contact comprises:
    impacting the surface with a laser beam from an excimer laser.

11. The method of claim 1, wherein contouring the surface of the at least one electrode contact comprises:
    chemically etching the at least one electrode contact.

12. The method of claim 1, wherein contouring the surface of the at least one electrode contact comprises:
    applying electric discharges between an electrode discharge machine (EDM) cutting tool and the at least one electrode contact.

13. The method of claim 1, wherein contouring the surface of the at least one electrode contact comprises:
    applying an acidic wash to the at least one electrode surface.

14. The method of claim 3, wherein removing the protective coating from the at least one electrode contact, comprises:
    dissolving the protective coating.

15. A system for manufacturing an electrode assembly comprising:
- means for contouring the surface of at least one electrode contact, so as to increase an effective surface area of the electrode contact surface without increasing the geometric surface area of the electrode contact comprising means for contouring a biocompatible substrate to form at least one designated electrode contact area having indentations formed therein;
- means for depositing a protective coating on the contoured surface;
- means for molding a carrier member about the at least one electrode contact, wherein the surface of the at least one electrode contact is covered by a layer of the carrier member material;
- means for cutting the coating around each designated electrode contact area; and
- means for removing the protective coating and the layer of carrier member material from the surface of the at least one electrode contact, comprising means for removing the coating from the regions of the substrate outside each designated electrode contact area.

16. The system of claim 15, further comprising:
- means for punching a comb from the substrate, the comb comprising at least one comb tooth comprising a designated electrode contact area; and
- means for shaping the comb to form at least one u-shaped electrode contact, each u-shaped electrode contact comprising one at least one contoured designated electrode contact area.

17. The system of claim 15:
- wherein means for contouring comprises means for contouring a biocompatible substrate to form at least one designated electrode contact area, each designated electrode contact area having a plurality of indentations formed therein; and
- wherein means for depositing comprises means for depositing a dissolvable layer of material on the contoured substrate;
- the system further comprising:
  - means for cutting the layer around each designated electrode contact area; and
  - means for removing the layer from the regions of the substrate outside each designated electrode contact area.

18. The system of claim 17, further comprising:
- means for punching a comb from the substrate, the comb comprising at least one comb tooth comprising a designated electrode contact area; and
- means for shaping the comb to form at least one u-shaped electrode contact, each u-shaped electrode contact comprising one at least one contoured designated electrode contact area.

19. The system of claim 15, wherein the means for depositing a protective coating on the contoured surface comprises:
- means for depositing a parylene layer on the contoured surface.

20. The system of claim 15, wherein the means for contouring the surface comprises:
- means for forming a pattern of indentations such that the effective surface area per area unit of a region of the surface outside the center region decreases from the center region towards edges of the at least one electrode contact.

21. The system of claim 15, wherein the means for contouring the surface comprises:
- means for modifying one or more portions of the surface outside of the center region such that each portion has a different effective surface area per area unit, wherein the portion adjacent the center region has a greater effective surface area per area unit than any other of the one or more portions.

22. The system of claim 15, wherein the means for contouring the surface of the at least one electrode contact comprises:
- means for laser ablating the surface of at least one electrode contact.

23. The system of claim 22, wherein the means for laser ablating the surface of the at least one electrode contact comprises:
- means for impacting the surface with a laser beam from an excimer laser.

24. The system of claim 15, wherein the means for contouring the surface of the at least one electrode contact comprises:
- chemically etching the at least one electrode contact.

25. The system of claim 15, wherein the means for contouring the surface of the at least one electrode contact comprises:
- means for applying electric discharges between an electrode discharge machine (EDM) cutting tool and the at least one electrode contact.

26. The system of claim 15, wherein the means for contouring the surface of the at least one electrode contact comprises:
- means for applying an acidic wash to the at least one electrode surface.

27. The system of claim 17, wherein the means for removing the protective coating from the at least one electrode contact, comprises:
- means for dissolving the protective coating.

28. A method for manufacturing an electrode assembly, the method comprising:
- contouring the surface of at least one electrode contact, so as to increase an effective surface area of the electrode contact surface without increasing the geometric surface area of the electrode contact;
- depositing a protective coating on the contoured surface;
- molding a carrier member about the at least one electrode contact, wherein the surface of the at least one electrode contact is covered by a layer of the carrier member material; and
- removing the protective coating and the layer of carrier member material from the surface of the at least one electrode contact,
  - wherein the contouring comprises:
    - contouring the surface of at least one electrode contact such that the effective surface area per area unit of a center region of the at least one electrode contact is larger than the effective surface area per area unit of the of the region of the surface outside the center region.

29. A method for manufacturing an electrode assembly, the method comprising:
- contouring the surface of at least one electrode contact, so as to increase an effective surface area of the electrode contact surface without increasing the geometric surface area of the electrode contact;
- depositing a protective coating on the contoured surface;

molding a carrier member about the at least one electrode contact, wherein the surface of the at least one electrode contact is covered by a layer of the carrier member material; and removing the protective coating and the layer of carrier member material from the surface of the at least one electrode contact, wherein the contouring the surface of the at least one electrode contact comprises one of the following: laser ablating the surface of at least one electrode contact, chemically etching the at least one electrode contact, applying electric discharges between an electrode discharge machine (EDM) cutting tool and the at least one electrode contact, and applying an acidic wash to the at least one electrode surface.

30. A system for manufacturing an electrode assembly comprising:

means for contouring the surface of at least one electrode contact, so as to increase an effective surface area of the electrode contact surface without increasing the geometric surface area of the electrode contact;

means for depositing a protective coating on the contoured surface;

means for molding a carrier member about the at least one electrode contact, wherein the surface of the at least one electrode contact is covered by a layer of the carrier member material; and means for removing the protective coating and the layer of carrier member material from the surface of the at least one electrode contact, wherein the means for contouring comprises means for contouring a biocompatible substrate to form at least one designated electrode contact area, each designated electrode contact area having a plurality of indentations formed therein;

the system further comprising:

means for removing the coating from the regions of the substrate outside each designated electrode contact area.

* * * * *